United States Patent
Kim et al.

(10) Patent No.: US 11,173,341 B2
(45) Date of Patent: Nov. 16, 2021

(54) WEARABLE APPARATUS AND USER TERMINAL DEVICE CONNECTABLE TO WEARABLE DEVICE

(71) Applicant: Samsung Electronics Co., Ltd., Suwon-si (KR)

(72) Inventors: Yong Kim, Seoul (KR); Eung-sun Kim, Seoul (KR); Jae-geol Cho, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 72 days.

(21) Appl. No.: 15/781,654

(22) PCT Filed: Aug. 9, 2016

(86) PCT No.: PCT/KR2016/008726
§ 371 (c)(1),
(2) Date: Jun. 5, 2018

(87) PCT Pub. No.: WO2017/111248
PCT Pub. Date: Jun. 29, 2017

(65) Prior Publication Data
US 2018/0353810 A1 Dec. 13, 2018

(30) Foreign Application Priority Data
Dec. 24, 2015 (KR) .................. 10-2015-0186554

(51) Int. Cl.
*G01D 1/00* (2006.01)
*A63B 24/00* (2006.01)
(Continued)

(52) U.S. Cl.
CPC ............ *A63B 24/0062* (2013.01); *A61B 5/01* (2013.01); *A61B 5/024* (2013.01); *A61B 5/1116* (2013.01);
(Continued)

(58) Field of Classification Search
CPC ............ A63B 24/0062; A63B 24/0006; A63B 2024/0071; A63B 2220/836; A61B 5/01;
(Continued)

(56) References Cited

U.S. PATENT DOCUMENTS 7,264,554 B2 9/2007 Bentley
2006/0166737 A1 7/2006 Bentley
(Continued)

FOREIGN PATENT DOCUMENTS

JP 2013-048720 A 3/2013
JP 2015-116288 A 6/2015
(Continued)

OTHER PUBLICATIONS

Extend European Search Report dated Oct. 1, 2018 issued in EP Application 16879116.8.
(Continued)

*Primary Examiner* — Aditya S Bhat
(74) *Attorney, Agent, or Firm* — Jefferson IP Law, LLP

(57) ABSTRACT

A wearable apparatus is disclosed. The wearable apparatus includes: a sensor for detecting a motion of the wearable apparatus; and a processor for extracting a motion pattern on the basis of the motion detected by the sensor, comparing a preselected motion pattern with the extracted motion pattern, and counting the number of times of motion corresponding to the preselected motion pattern.

15 Claims, 24 Drawing Sheets

(51) Int. Cl.
  *A61B 5/01*        (2006.01)
  *A61B 5/024*       (2006.01)
  *H04B 5/00*        (2006.01)
  *A61B 5/00*        (2006.01)
  *A61B 5/11*        (2006.01)
  *A61B 5/053*       (2021.01)

(52) U.S. Cl.
  CPC ........... *A61B 5/1118* (2013.01); *A61B 5/1122* (2013.01); *A61B 5/1123* (2013.01); *A61B 5/486* (2013.01); *A61B 5/681* (2013.01); *A63B 24/0006* (2013.01); *H04B 5/00* (2013.01); *A61B 5/053* (2013.01); *A61B 2503/10* (2013.01); *A61B 2505/09* (2013.01); *A61B 2562/0219* (2013.01); *A63B 2024/0071* (2013.01); *A63B 2220/836* (2013.01)

(58) Field of Classification Search
  CPC ..... A61B 5/024; A61B 5/1116; A61B 5/1118; A61B 5/1122; A61B 5/1123; A61B 5/486; A61B 5/681; A61B 5/053; A61B 2503/10; A61B 2505/09; A61B 2562/0219; H04B 5/00
  USPC .......................................... 702/127
  See application file for complete search history.

(56) References Cited

U.S. PATENT DOCUMENTS

| | | | |
|---|---|---|---|
| 2007/0219059 | A1 | 9/2007 | Schwartz et al. |
| 2014/0278220 | A1* | 9/2014 | Yuen ................. A61B 5/02427 702/150 |
| 2015/0172441 | A1* | 6/2015 | Samhat ................. H04M 1/663 455/418 |
| 2015/0230719 | A1* | 8/2015 | Berg ........................ A61B 5/04 600/388 |
| 2016/0131677 | A1* | 5/2016 | Bostick .............. G06K 9/00335 73/865.4 |
| 2017/0039480 | A1* | 2/2017 | Bitran .................... G06N 20/00 |
| 2021/0128979 | A1* | 5/2021 | McHugh .............. A63B 21/078 |

FOREIGN PATENT DOCUMENTS

| | | |
|---|---|---|
| KR | 10-2007-0095407 A | 9/2007 |
| KR | 10-2013-0036569 A | 4/2013 |
| KR | 10-2013-0045382 A | 5/2013 |
| KR | 10-2014-0097186 A | 8/2014 |
| KR | 10-2014-0133685 A | 11/2014 |
| KR | 10-2015-0020659 A | 2/2015 |
| KR | 10-2015-0043531 A | 4/2015 |
| KR | 10-2015-0089522 A | 8/2015 |
| KR | 10-2015-0112741 A | 10/2015 |
| WO | 2012-021507 A2 | 2/2012 |
| WO | 2013-063159 A2 | 5/2013 |
| WO | 2013-184672 A2 | 12/2013 |
| WO | 2015/034824 A1 | 3/2015 |

OTHER PUBLICATIONS

Korean Office Action dated Jun. 18, 2020, issued in Korean Patent Application No. 10-2015-0186554.
Korean Office Action dated Dec. 28, 2020, issued in Korean Patent Application No. 10-2015-0186654.
European Search Report dated Mar. 11, 2021, issued in European Patent Application No. 16 879 116.8.

* cited by examiner

FIG. 7
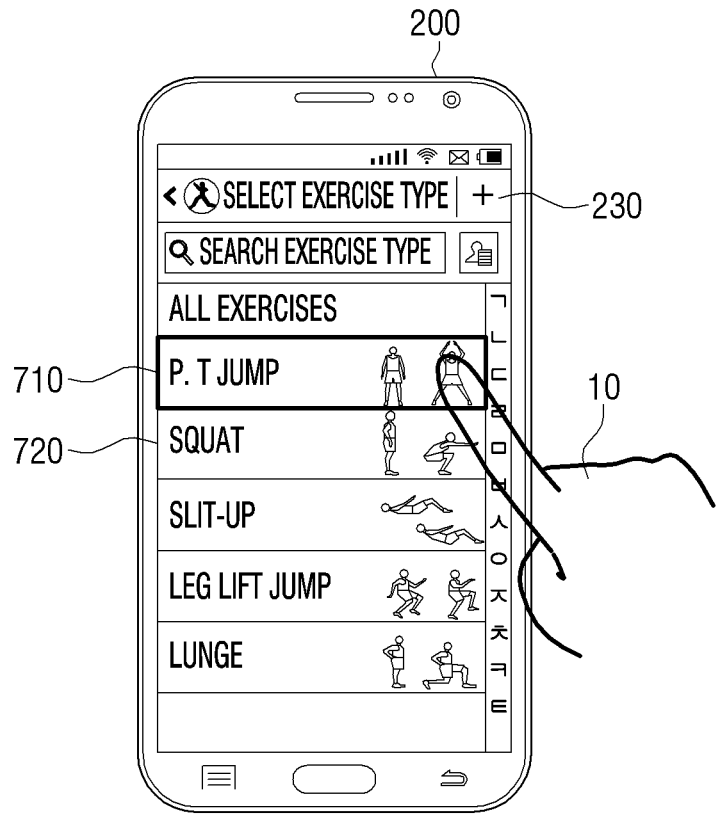
(a)
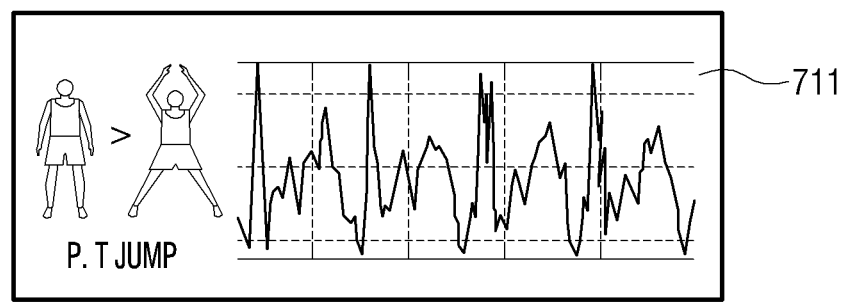
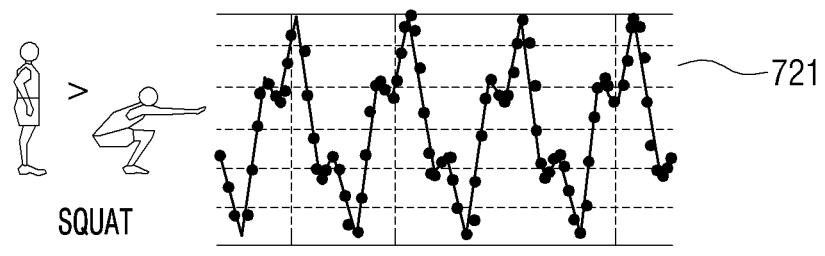
(b)

FIG. 11

| POSTURE CLASSIFICATION | CONTENTS |
|---|---|
| GOOD PERFORMING POSTURE (GOOD) | COMPLETE THAT POSTURE IS PERFORMED WITHIN TIME LIMIT |
| NORMAL PERFORMING POSTURE (NORMAL) | - NOISE PATTERN APPEAR AT THE TIME OF PERFORMING POSTURE<br>- POSTURE IS PERFORM OVER TIME LIMIT |
| BAD PERFORMING POSTURE (BAD) | PATTERN IN WHICH POSTURE IS PERFORMED IS COMPLETELY DIFFERENT |

(a)    (b)

WEARABLE APPARATUS AND USER TERMINAL DEVICE CONNECTABLE TO WEARABLE DEVICE

CROSS-REFERENCE TO RELATED APPLICATION(S)

This application is a U.S. National Stage application under 35 U.S.C. § 371 of an International application number PCT/KR2016/008726, filed on Aug. 9, 2016, which is based on and claimed priority of a Korean patent application number 10-2015-0186554, filed on Dec. 24, 2015, in the Korean Intellectual Property Office, the disclosure of which is incorporated by reference herein in its entirety.

TECHNICAL FIELD

The present disclosure relates to a wearable device and a user terminal device connectable to the wearable device, and more particularly, to a wearable device capable of confirming an exercise state of a user by sensing a motion of the wearable device, and a user terminal device connectable to the wearable device.

BACKGROUND ART

With advances in medical technology, as human life has increased significantly, the need for continuous health care through exercise has emerged. Many people are exercising individually at home or on the playground as well as in health clubs equipped with professional exercise equipments for health care. Accordingly, devices equipped with an exercise helper function that measures an amount of exercise of the user and provides a calorie consumption amount are recently released. However, the devices which are currently released are limited to walking, running, and the like to which an average amount of exercise per hour may be substituted, and only provide an approximate amount of exercise or calorie consumption amount. In addition, there is a disadvantage that people who exercise alone without the help of an expert do not know whether they are exercising in the right posture or exercising with appropriate intensity.

Accordingly, there is a need for a technique for presenting an exercise which suits the user and confirming and recording an exercise state of the user to effectively perform the health care through the exercise.

DISCLOSURE

Technical Problem

An object of the present disclosure is to provide a wearable device capable of confirming an exercise state of a user using a pattern extracted from a sensed motion of the wearable device, and a user terminal device connectable to the wearable device.

Technical Solution

According to an aspect of the present disclosure, a wearable device includes a sensor configured to sense a motion of the wearable device; and a processor configured to extract a motion pattern based on the motion sensed by the sensor, compare a preselected exercise pattern with the extracted motion pattern, and count the number of times that exercise corresponding to the preselected exercise pattern is performed.

The processor may compare the predetermined exercise pattern with the extracted motion pattern and determine an accuracy of the exercise.

The wearable device may further include a user interface configured to be selected with exercise, wherein the processor may compare an exercise pattern corresponding to the selected exercise with the extracted motion pattern.

The user interface may display the counted number of times that the exercise is performed.

The user interface may display together the counted number of times that the exercise is performed and the prestored target number of times.

The processor may modify the prestored target number of times based on the number of times that the exercise is performed for a predetermined time.

The wearable device may further include a communicator receiving exercise information from an external device, wherein the processor may compare an exercise pattern corresponding to the exercise information with the extracted motion pattern.

The exercise information may include at least one of exercise selected by a user and an exercise pattern corresponding to the exercise selected by the user.

The processor may control the communicator to transmit the counted number of times that the exercise is performed to the external device.

The communicator may include a near filed communication (NFC) module communicable with an NFC tag.

The sensor includes at least one of a three-axis acceleration sensor and a gyro sensor.

The wearable device may further include a body contact sensor measuring biological signals of a user, the processor may calculate an exercise effect of the exercise based on the measured biological signals of the user.

The body contact sensor may include at least one of a heartbeat measuring sensor, a body temperature measuring sensor, and a skin resistance sensor.

According to another aspect of the present disclosure, a user terminal device connectable to a wearable device includes a communicator configured to receive motion information from the wearable device; and a processor configured to extract a motion pattern of the wearable device using the received motion information, comparing a preselected exercise pattern with the extracted motion pattern, and counting the number of times that exercise corresponding to the reselected exercise pattern is performed.

The processor may compare the predetermined exercise pattern with the extracted motion pattern and determine an accuracy of the exercise.

The user terminal device may further include a user interface configured to be selected with exercise, wherein the processor may compare an exercise pattern corresponding to the selected exercise with the extracted motion pattern.

The user interface may display the counted number of times that the exercise is performed.

The user interface may display together the counted number of times that the exercise is performed and the prestored target number of times.

The processor may modify the prestored target number of times based on the number of times that the exercise is performed for a predetermined time.

The communicator may further receive biological signals of a user from the wearable device and the processor may calculate an exercise effect of the exercise based on the received biological signals of the user.

DESCRIPTION OF DRAWINGS

FIGS. 7 and 8 are diagrams illustrating a method for limiting a pattern to be compared with a measured motion of the user.

FIG. 11 is a diagram illustrating a method for determining an exercise posture of a user according to an exemplary embodiment of the present disclosure.

BEST MODE

Figure 1:
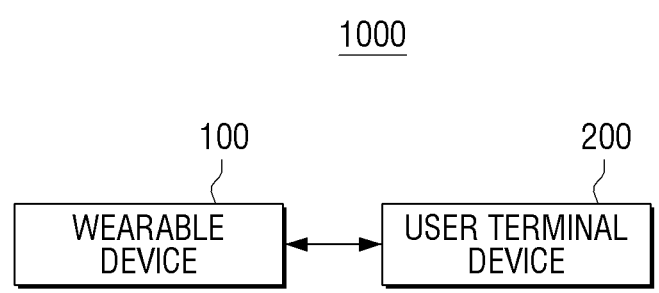
FIG. 1 is a drawing illustrating a configuration of an exercise management system of a user using a wearable device according to an exemplary embodiment of the present disclosure.

The exemplary embodiments of the present disclosure may be diversely modified. Accordingly, specific exemplary embodiments are illustrated in the drawings and are described in detail in the detailed description. However, it is to be understood that the present disclosure is not limited to a specific exemplary embodiment, but includes all modifications, equivalents, and substitutions without departing from the scope and spirit of the present disclosure. In describing the exemplary embodiments, when it is determined that a specific description of known technologies would obscure the gist of the present disclosure, a detailed description thereof will be omitted.

Terms such as first, second, etc. can be used to describe various components, but the components should not be limited to the terms. The terms are only used to distinguish one component from the others.

The terms used in the present application are only used to describe the exemplary embodiments, but are not intended to limit the scope of the present disclosure. As used herein, the singular forms are intended to include plural forms as well, unless the context clearly indicates otherwise. In the present application, the terms "include" or "consist of" intend to designate the presence of features, numbers, steps, operations, components, elements, or a combination thereof that are written in the specification, but do not exclude the presence or possibility of addition of one or more other features, numbers, steps, operations, components, elements, or a combination thereof.

In the exemplary embodiment of the present disclosure, a 'module' or a 'unit' performs at least one function or operation, and may be implemented in hardware, software, or a combination of hardware and software. In addition, a plurality of 'modules' or a plurality of 'units' may be integrated into at least one module and may be implemented in at least one processor (not shown), except for a 'module' or a 'unit' in which they need to be implemented in specific hardware.

Hereinafter, the present disclosure will be described in more detail with reference to the accompanying drawings.

FIG. 1 is a drawing illustrating a configuration of an exercise management system of a user using a wearable device according to an exemplary embodiment of the present disclosure.

Referring to FIG. 1, an exercise management system 1000 of a user using a wearable device according to an exemplary embodiment of the present disclosure includes a wearable device 100 mounted on a body of the user and a user terminal device 200.

In this case, the wearable device 100 may be mounted on the body of the user to measure a motion of the user. In this case, the measuring of the motion of the user may refer to sensing a motion of the wearable device 100 using a sensor provided inside the wearable device 100, and extracting a motion pattern of the user based on the sensed motion.

Meanwhile, the wearable device 100 may compare a pattern of a preselected exercise with the extracted motion pattern of the user, and count the number of times that the user performs exercise corresponding to the pattern of the preselected exercise.

Meanwhile, although the wearable device 100 is described as being one for convenience of explanation, the motion of the user may be measured using a plurality of wearable devices 100 at the time of actual implementation.

In addition, the wearable device 100 may further include a sensor for measuring biological signals such as heartbeat, body temperature, skin resistance, and the like of the user to measure the biological signals of the user and to calculate an exercise effect of the user.

Meanwhile, a detailed configuration of the wearable device 100 will be described below in detail with reference to FIG. 2.

Meanwhile, the user terminal device 200 may be connected to the wearable device 100 and display an exercise result measured by the wearable device 100. Specifically, the user terminal device 200 may display the exercise result transmitted from the wearable device 100.

Meanwhile, the user terminal device 200 may receive motion information of the wearable device 100 sensed from the wearable device 100 to extract the motion pattern of the user. In this case, the user terminal device 200 may compare a pattern of the preselected exercise with the extracted motion pattern of the user, and count the number of times that the user performs exercise corresponding to the pattern of the preselected exercise. In this case, the user terminal device 200 may display the counted number of times that the exercise is performed.

As described above, the exercise management system 1000 of the user according to the present exemplary embodiment may sense the motion of the wearable device 100 mounted on the body of the user and count the number of times that the user performs the preselected exercise.

Meanwhile, in describing FIG. 1, although the respective components are illustrated and described as being connected directly to each other, the respective devices may be implemented in a form in which they are directly connected to each other and are indirectly connected to each other through a router, other devices (e.g., a server), or the like at the time of implementation.

Figure 2:
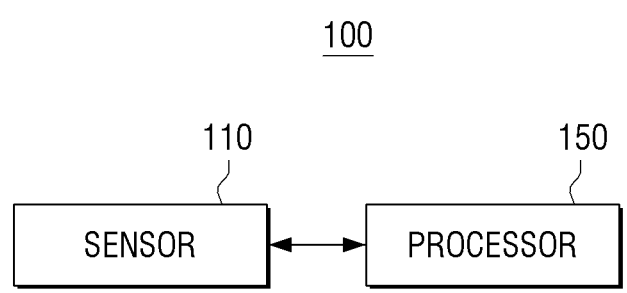
FIG. 2 is a block diagram illustrating a simplified configuration of the wearable device of FIG. 1.

FIG. 2 is a block diagram illustrating a simplified configuration of the wearable device of FIG. 1.

The wearable device 100 of FIG. 2 may be a smart watch in the form of a wristwatch having a sensor for measuring a motion of a user. However, the wearable device 100 is not limited thereto, but may be a band type device having a sensor and being able to fit in a part of the body of the user at the time of actual implementation. Meanwhile, for convenience of explanation, the wearable device 100 will be described below as being limited to the form of the wristwatch.

Referring to FIG. 2, the wearable device 100 may include a sensor 110 and a processor 150.

The sensor 110 may sense a motion of the wearable device 100. Specifically, the sensor 110 may be disposed inside the wearable device 100 and sense a motion of the wearable device 100. In this case, the sensor 110 may include at least one of an acceleration sensor and a gyro sensor. In this case, the acceleration sensor may be a three-axis acceleration sensor.

In this case, the acceleration sensor may measure dynamic forces such as acceleration, vibration, impact, and the like of an object. In this case, the three-axis acceleration sensor may measure the dynamic forces of the object by dividing into an x axis, a y axis, and a z axis.

Meanwhile, the gyro sensor may be technology utilized for position measurement and direction setting, using dynamic motion of a rotating object. Specifically, the gyro sensor may be sensor that measures a change in an azimuth of the object using a property that always maintains a constant direction which is initially set at high accuracy regardless of the rotation of the earth.

Meanwhile, the processor 150 controls the respective configurations in the wearable device 100. Specifically, if one exercise of a plurality of exercises is selected by the user, the processor 150 may control the sensor 110 to sense the motion of the wearable device 100 mounted on the body of the user. Specifically, if the wearable device 100 moves, the processor 150 may control the sensor 110 to continuously sense the motion. Meanwhile, even if the wearable device 100 does not move, the processor 150 may control the sensor 110 to periodically sense the motion.

Meanwhile, if a plurality of sensors 110 are present in the wearable device 100, the processor 150 may control to turn on/off a power source of each of the plurality of sensors.

In this case, the processor 150 may count the number of times that the user performs the preselected exercise using the motion sensed by the sensor 110. Specifically, the processor 150 may extract a motion pattern based on the motion of the wearable device 100 sensed by the sensor 110. In this case, the processor 150 may compare a pattern of the preselected exercise with the extracted motion pattern of the user, and count the number of times that the user performs exercise corresponding to the pattern of the preselected exercise. In this case, the pattern of the preselected exercise may be any one of a pattern of exercise selected by the user among a plurality of exercise patterns stored in the wearable device 100, an exercise pattern received by the user terminal device, or an exercise pattern selected by an NFC tag. The selection of the exercise pattern by the user will be described in detail with reference to FIG. 7.

Meanwhile, the processor 150 may divide the motion of the wearable device 100 sensed by the three-axis acceleration sensor by each axis and compare it with the pattern of the preselected exercise. Meanwhile, the processor 150 may calculate the magnitude of the motion of the wearable device 100 sensed by the acceleration sensor and also compare it with the pattern of the preselected exercise.

Meanwhile, the processor 150 may count the number of times of swings using the gyro sensor. For example, the processor 150 may count the number of times that the user swings using the instrument as in golf, badminton, tennis, baseball, and the like. In this case, the processor 150 may further use the acceleration sensor to measure the impact of the instrument upon striking.

Meanwhile, hereinabove, although only simple configurations configuring the wearable device 100 have been illustrated and described, various configurations may be additionally included at the time of implementation. This will be described in detail with reference to FIG. 3.

Figure 3:
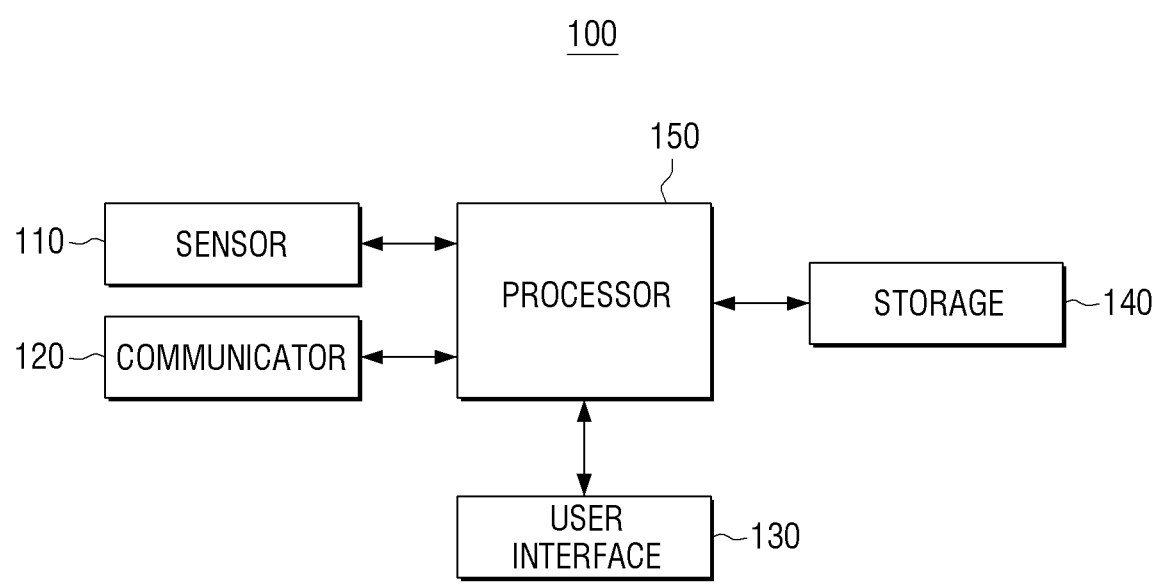
FIG. 3 is a block diagram illustrating a detailed configuration of the wearable device of FIG. 1.

FIG. 3 is a block diagram illustrating a detailed configuration of the wearable device of FIG. 1.

Referring to FIG. 3, the wearable device 100 may include a sensor 110, a communicator 120, a user interface 130, a storage 140, and a processor 150.

The sensor 110 may further include a body contact sensor that measures biological signals in addition to the three-axis acceleration sensor or the gyro sensor. Specifically, the sensor 110 may further include at least one of a heartbeat measuring sensor, a body temperature measuring sensor, and a skin resistance sensor.

In this case, the sensor 110 may be included in the wearable device 100 to measure the biological signals of the user before exercise, after exercise, and during exercise. As a result, the wearable device 100 may calculate an exercise effect of the user by comparing the biological signals of the user before and after exercise.

Meanwhile, hereinabove, although the sensor 110 provided to sense the motion of the wearable device 100 is described as being limited to at least one of the three-axis acceleration sensor and the gyro sensor, the motion of the wearable device 100 may be sensed by an infrared ray sensor, a camera, an illumination sensor, and the like at the time of implementation.

The communicator 120 is formed to connect the wearable device 100 to an external device, and may be connect to the external device via a local area network (LAN) and an Internet network as well as by a wireless communication scheme (e.g., Global System for Mobile Communications (GSM), Universal Mobile Telephone System (UMTS), Long-Term Evolution (LTE), WiBRO, or the like). Specifically, the communicator 120 may be formed to connect at least one of the user terminal device and the server, which are the external devices, to the wearable device 100.

The communicator 120 may receive information on the preselected exercise from the external device. In this case, the exercise information may include at least one of exercise selected by the user and an exercise pattern corresponding to the exercise selected by the user. Specifically, in a case in which a plurality of exercise patterns are stored in the wearable device 100, if user selects one exercise of the plurality of exercises in the external device, the communicator 120 may receive only exercise selection information corresponding to the selected one exercise, and in a case in which the plurality of exercise patterns are not stored in the wearable device 100, the communicator 120 may receive an exercise pattern corresponding to the exercise selected by the user in the external device.

Meanwhile, the communicator 120 may include a near field communication (NFC) module. Specifically, the communicator 120 may include the NFC module which is able to communicate with an external device on which the NFC tag is mounted. In this case, the NFC refers to a technology that transits data between terminals at a close distance of 10 cm, using a non-contact short range wireless communication module that uses a frequency band of 13.56 MHz as one of radio frequency identification (RFID).

For example, if the user exercises in a fitness center equipped with health instruments on which the NFC tag is mounted, the user may tag his or her wearable device with the selected health instrument to allow the wearable device 100 to count the number of times of exercise of the corresponding health instrument.

Meanwhile, a method for counting the number of time of exercise of the corresponding health instrument using the NFC tag will be described below in detail with reference to FIG. 19.

Meanwhile, hereinabove, although the communication between the wearable device 100 and the health instrument is illustrated and described as being limited to being performed by the NFC tag, various communication schemes such as Bluetooth Low Energy (BLE), Wireless Fidelity (Wi-Fi), visible light communication, and the like may be used at the time of actual implementation.

In this case, the BLE means a Bluetooth scheme that operates at a low power. The BLE has characteristics that in order to increase efficiency of the use of the power source of the device, it reduces an operating cycle such that it sleeps for a longer time, is less activated, transmits a smaller data packet for a shorter time, and does not maintain a line while not performing communication.

In addition, the Wi-Fi is a technology that refers to a local area network capable of implementing wireless Internet within a predetermined distance using a radio wave or an infrared ray transmission scheme in a place in which an access point (AP) is installed.

In addition, the visible light communication is a visible light communication (VLC) technology capable of transmitting and receiving data using a radio wave discharged from a light emitting diode (LED), and may be used wherever lighting is available, and is harmless to the body and inexpensive. Since the visible communication may communicate even at LED illuminance which may not be seen with the naked eye, does not have a problem such as frequency confusion, and the like, and may provide a high-speed communication service at low cost, it is evaluated as a technology that may replace public Wi-Fi and significantly improve Internet accessibility. Meanwhile, hereinafter, for convenience of explanation, the communication between the wearable device 100 and the health instrument is illustrated and described by being limited to be performed by the NFC tag.

Meanwhile, the communicator 120 may transmit the number of times of exercise counted based on the motion sensed by the sensor 110 and the exercise effect information calculated based on the biological signals of the user sensed by the sensor 110 to the external device.

Meanwhile, the communicator 120 may transmit the motion or the biological signals of the user sensed by the sensor 110 to the external device. By immediately transmitting the measured information to the external device without a process of processing the signal and the biological signals sensed by the wearable device 100, the exercise management system according to the present disclosure may be implemented even in the case in which the wearable device 100 does not include a large capacity battery and a large capacity memory.

The user interface 130 may display a plurality of exercises and may be selected with one of the plurality of displayed exercises. Specifically, the user interface 130 may be a touch screen that displays the plurality of exercises and may receive the selection of the user, or a button, a wheel, a dial, or the like that may select one of the plurality of exercises, when the plurality of exercises are displayed on a separate display included in the wearable device. Hereinafter, the user interface 130 according to the present disclosure will be illustrated and described as being limited to the touch screen.

In this case, an example of a user interface window which may be displayed will be described below with reference to FIG. 7. Meanwhile, if the user interface 130 is selected with one exercise, the user interface 130 may display a right execution posture of the selected exercise. In this case, the user interface 130 may display the right execution posture of the selected exercise in the form of GIF, AVI, JPG, and JPEG.

Meanwhile, the user interface 130 may display at least one of a time limit and a target number of times to perform exercise together with the right execution posture of the selected exercise. In this case, after the user interface 130 displays at least one of the right execution posture, the time limit, and the target number of times of the selected exercise, if there is a touch of the user or a predetermined time has elapsed, the user interface 130 may display at least one of the remaining time of the time limit and the counted number of times of execution.

Meanwhile, if the exercise of the user is completed, the user interface 130 may display the counted number of times of execution and the number of times that the exercise is performed in a right posture. In this case, the user interface 130 may further display the calculated exercise effect such as an amount of calorie consumption, a change in body temperature, a change in heartbeat, a change in skin resistance, and the like. In this case, an example of a user interface window which may be displayed will be described below in detail with reference to FIG. 13. Meanwhile, hereinabove, although the user interface 130 is described as being limited to the touch screen, the user interface 130 may also be implemented by a scheme of providing the counted number of times of execution to the user using the LED, a mechanical type needle, or the like included in the wearable device 100 at the time of implementation.

Meanwhile, the user interface 130 may receive the selection of the user and display the user interface window for displaying the exercise result, as described above. The user interface 130 may be implemented in various forms of displays such as a liquid crystal display (LCD), organic light emitting diodes (OLED) display, a plasma display panel (PDP), and the like. The user interface 130 may include a driving circuit, a backlight unit, and the like which may be implemented in the forms such as an a-si TFT, a low temperature poly silicon (LTPS) TFT, an organic TFT (OTFT), and the like. In addition, the user interface 130 may also be implemented as a flexible display.

Meanwhile, the user interface 130 may include a touch sensor for sensing a touch gesture of the user. The touch sensor may be implemented as various types of sensors such as a capacitive sensor, a resistive sensor, a piezoelectric sensor, and the like. The capacitive type means a scheme calculating a touch coordinate by sensing micro-electricity exited into a body of the user when a portion of the body of the user touches a surface of the touch screen, using a dielectric coated on the surface of the touch screen. The resistive type means a scheme including two electrode plates embedded in the touch screen and calculating the touch coordinate by sensing that upper and lower plates of a touched point are in contact with each other to allow a current to flow, when the user touches the screen. Besides, in the case in which the wearable device 100 also supports a pen input function, the user interface 130 may also sense a user gesture using an input means such as a pen other than a finger of the user. In the case in which the input means is a stylus pen including a coil, the wearable device 100 may also include a magnetic field sensing sensor capable of a magnetic field which is changed by the coil in the stylus pen. Accordingly, the user interface 130 may also sense an adjacent gesture, that is, a hovering as well as the touch gesture.

Meanwhile, hereinabove, although one user interface 130 is described as performing both a display function and a function of sensing the touch gesture, the display function and the function of sensing the gesture may be performed in different configurations at the time of implementation, That is, the user interface 130 may also be implemented by combining a display device capable of displaying only an image and a touch panel capable of sensing only a touch. Meanwhile, at the time of actual implementation, the user interface 130 may also implemented by a scheme in which the plurality of exercises are displayed on the display capable of displaying the image and one of the plurality of exercises is selected by a button, a dial, a wheel, or the like.

The storage 140 may store a variety of programs and data necessary to operate the wearable device 100. Specifically, the storage 140 may store the program, the data, and the like for configuring a variety of UIs configuring the user interface window.

In addition, the storage 140 stores a variety of contents. Here, the contents may be a pattern of the selected exercise received from the external device. Meanwhile, the contents may be a plurality of exercise patterns, an image corresponding to each of the exercise patterns, and an image of a right exercise posture.

In addition, the storage 140 may store at least one of the motion sensed by the sensor 110 and the motion pattern extracted based on the sensed motion. In addition, the storage 140 may compare the pattern of the selected exercise with the extracted motion pattern and store the counted number of times of execution of the exercise.

In addition, the storage 140 may store the biological signals of the user measured by the sensor 110 and the exercise effect information calculated based on the measured biological signals.

The processor 150 may display the user interface window on the user interface 130 using the programs and the data stored in the storage 140. In addition, if the user touches a specific region of the user interface window, the processor 150 may perform a control operation corresponding to the touch. Specifically, the processor 150 may control the interface 130 to display the plurality of exercises and to be selected with one of the plurality of displayed exercises. In this case, if the user selects one exercise, the processor 150 may control the user interface 130 to display the right posture of the selected exercise and display a time limit and a target number of times together with the right posture.

Meanwhile, the processor 150 may control the sensor 110 to measure the biological signals of the user, in addition to control the sensor 110 to sense the motion of the wearable device 100.

Meanwhile, the processor 150 may control the communicator 120 to receive the preselected exercise information from the external device. In this case, the exercise information may include at least one of exercise selected by the user in the external device and an exercise pattern corresponding to the exercise selected by the user.

Meanwhile, if the communicator 120 including the NFC module tags with the external device on which the NFC tag is mounted, the processor 150 may control the communicator 120 to receive information corresponding to the tagged external device from the external device.

Meanwhile, the processor 150 may extract a pattern from the motion of the wearable device 100 sensed by the sensor 110. In this case, the processor 150 may compare the extracted motion pattern with the pattern of the preselected exercise, and count the number of times that the user performs exercise corresponding to the corresponding exercise pattern. In this case, the processor 150 may compare the extracted motion pattern with the pattern of the preselected exercise, and determine an accuracy of the exercise performed by the user. Specifically, the processor 150 may compare the extracted motion pattern with the pattern of the preselected exercise, and count the number of times that the exercise of the user is performed in the right posture. Meanwhile, a criterion for determining whether the user performs the exercise in the right posture will be described below with reference to FIGS. 11 and 12.

In this case, the processor 150 may update the prestored exercise pattern according to the determined posture that the user performs the exercise. Specifically, the processor 150 may compare the exercise pattern stored in a database with the extracted motion pattern of the user, and determine whether or not the exercise of the user is performed in the right posture. In this case, if a difference between the motion pattern and the exercise pattern of the user corresponds to a predetermined range, and the counted number of times corresponds to a predetermined value or more when the number of times corresponding to the predetermined range is counted, the processor 150 may update the prestored exercise pattern to suit the user.

For example, in the case in which it is present to perform one operation of the selected exercise for 5 seconds, but the user takes 6 seconds to perform the same operation and the number of times that the user takes 6 seconds to perform the operation is a predetermined value or more, the processor 150 may modify and store a target time to 6 seconds. Thereafter, if the user selects the same operation, the processor 150 may present to perform one operation for 6 seconds. Thereby, the wearable device 100 may adjust intensity of the exercise to suit the user and present the adjusted intensity. Meanwhile, a method for updating the prestored exercise pattern will be described below in detail with reference to FIG. 24.

Meanwhile, the processor 150 may control the sensor 110 to further measure the biological signals of the user before the user begins the exercise, during the exercise, and after the exercise, using a body contact sensor. In this case, the processor 150 may calculate the exercise effect of the user using the measured biological signals of the user. Specifically, the processor 150 may calculate the exercise effect such as an amount of calorie consumption, a change in body temperature, a change in heartbeat, and a change in skin resistance using at least one of heartbeat, body temperature, and skin resistance measured before and after the exercise.

Meanwhile, the processor 150 may control the user interface 130 to display the calculated exercise result. Specifically, the processor 150 may control the touch screen 130 to display the exercise effect such as the number of times that the user performs the exercise, the number of times that the user performs the exercise in the right posture, the amount of calorie consumption, and the like. In this case, an example of a user interface window which may be displayed will be described below in detail with reference to FIG. 13.

Meanwhile, the processor 150 may compare a time limit and the target number of times which are present before the user begins the exercise with the number of times that the user performs the exercise to modify the target number of times stored in the storage 140. For example, if the user completes the target number of times within the presented time limit, the processor 150 may increase the target number of times or reduce the time limit and may store the increased target number of times or the reduced time limit. Thereby, the wearable device 100 may present exercise of the adjusted intensity according to exercise ability of the user. Meanwhile, a method for modifying the exercise intensity according to the counted number of times that the exercise is performed will be described below in detail with reference to FIGS. 21 and 22.

Meanwhile, hereinabove, for convenience of explanation, although the description is made as being limited to a case in which one exercise is selected and the number of times that the selected exercise is performed, a program including a plurality of exercises may be selected and the number of times that the plurality of exercises included in the selected program are performed may be counted at the time of actual implementation. Meanwhile, a method for selecting the exercise program and counting the number of times that the plurality of exercises included in the exercise program are performed will be described below with reference to FIG. 23.

Figure 4:
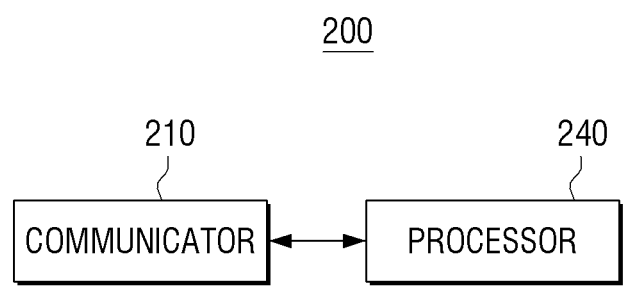
FIG. 4 is a block diagram illustrating a simplified configuration of the user terminal device of FIG. 1.

FIG. 4 is a block diagram illustrating a simplified configuration of the user terminal device of FIG. 1.

FIG. 4 is a block diagram illustrating a simplified configuration of the user terminal device of FIG. 1.

The user terminal device 200 of FIG. 4 may be specifically implemented as various kinds of devices such as a TV, a PC, a laptop PC, a cellular phone, a tablet PC, a PDA, an MP3 player, a kiosk, an electronic picture frame, and the like. When the user terminal device 200 is implemented as portable kinds of devices such as the cellular phone, the tablet PC, the PDA, the MP3 player, the laptop PC, and the like, the user terminal device 200 may also be referred to as a mobile device, but is collectively called the user terminal device in the present specification.

Referring to FIG. 4, the user terminal device 200 may include a communicator 210 and a processor 240.

The communicator 210 is formed to connect the user terminal device 200 to an external device, and may be connect to the external device via a local area network (LAN) and an Internet network as well as by a wireless communication scheme (e.g., Global System for Mobile Communications (GSM), Universal Mobile Telephone System (UMTS), Long-Term Evolution (LTE), WiBRO, or the like). Specifically, the communicator 210 may be formed to connect at least one of the wearable device and the server, which are the external devices, to the user terminal device 200.

The communicator 210 may transmit a pattern of preselected exercise to the external device. Specifically, in a case in which a plurality of exercise patterns are stored in the user terminal device 200, the communicator 210 may transmit the pattern of the preselected exercise to the wearable device or the server. Meanwhile, the communicator 210 may transmit information on a right execution posture of the preselected exercise together with the pattern of the preselected exercise to the external device.

Meanwhile, the communicator 210 may receive the pattern of the preselected exercise from the external device. Specifically, in a case in which the plurality of exercise patterns are not stored in the user terminal device 200, the communicator 210 may receive the pattern of the preselected exercise transmitted from the wearable device or the server. Meanwhile, the communicator 210 may receive information on a right execution posture of the preselected exercise together with the pattern of the preselected exercise from the external device.

Meanwhile, the communicator 210 may receive the motion of the wearable device and the biological signals sensed by the wearable device to count the number of times that the exercise is performed in the user terminal device and calculate the exercise effect.

Meanwhile, if the number of times that the user performs the exercise is counted in the user terminal device 200, the communicator 210 may transmit the counted number of times that the user performs the exercise to the external device. Meanwhile, if the number of times that the user performs the exercise is counted in the external device, the communicator 210 may receive the counted number of times that the user performs the exercise from the external device to display it.

The processor 240 controls the respective configurations in the user terminal device 200. Specifically, if one exercise of the plurality of exercises is selected by the user, the processor 240 may control the communicator 210 to transmit a pattern of the selected exercise to the external device.

Meanwhile, the processor 240 may count the number of time that the user performs the preselected exercise using motion information received from the external device. Specifically, the processor 240 may extract the motion pattern of the user based on the motion information received from the external device. In this case, the processor 240 may compare a pattern of the preselected exercise with the extracted motion pattern of the user, and count the number of times that the user performs exercise corresponding to the pattern of the preselected exercise. In this case, the pattern of the preselected exercise may be any one of a pattern of exercise selected by the user among a plurality of exercise patterns stored in the user terminal device 200, a pattern of the preselected exercise received from the server, or an exercise pattern selected by an NFC tag. The selection of the exercise pattern by the user will be described in detail with reference to FIG. 7.

Meanwhile, the processor 240 may receive motion information of the wearable device sensed by a three-axis acceleration sensor of the wearable device, divide the received motion information by each axis, and compare it with the pattern of the preselected exercise. Meanwhile, the processor 240 may receive the motion information of the wearable device sensed by the acceleration sensor, extract a pattern of the motion, calculate the magnitude of the extracted pattern, and also compare it with the pattern of the preselected exercise.

Meanwhile, the processor 240 may receive the motion information measured by the gyro sensor of the wearable device and count the number of times that the user swings. For example, the processor 240 may count the number of times that the user swings using the instrument as in golf, badminton, tennis, baseball, and the like. In this case, the processor 240 may further receive the motion information measured by the acceleration sensor of the wearable device to measure an impact of the device upon striking.

Meanwhile, hereinabove, although only simple configurations configuring the user terminal device 200 have been illustrated and described, various configurations may be additionally included at the time of implementation. This will be described in detail with reference to FIG. 5.

Figure 5:
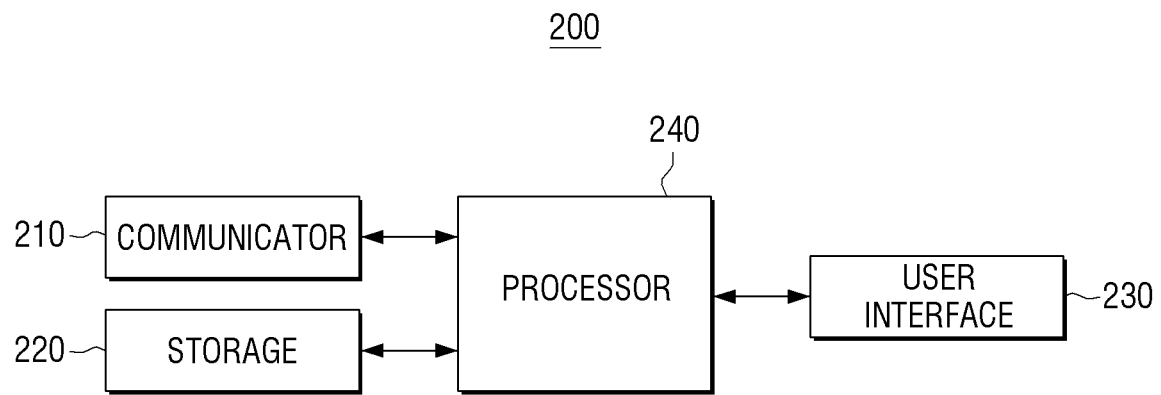
FIG. 5 is a block diagram illustrating a detailed configuration of the user terminal device of FIG. 1.

FIG. 5 is a block diagram illustrating a detailed configuration of the user terminal apparatus of FIG. 1.

Referring to FIG. 5, the user terminal device 200 may include a communicator 210, a storage 220, a user interface 230, and a processor 240.

The communicator 210 may receive the number of times counted by the external device to display the exercise result on the user terminal device 200. In addition, the communicator 210 may further receive the number of times that the user performs a preselected exercise posture in a right posture together with the counted number of times.

Meanwhile, the communicator 210 may further receive at least one of the biological signals of the user and the exercise effect calculated based on the biological signals from the wearable device. Specifically, the communicator 210 may receive information on heartbeat, body temperature, and skin resistance of the user which are measured by the external device, or receive an amount of calorie consumption, a change in body temperature, a change in heartbeat, a change in skin resistance, and the like calculated based on the biological signals of the user.

The storage 220 may store a variety of programs and data which are required to operate the user terminal device 200. Specifically, the storage 220 may store the program, the data, and the like for configuring a variety of UIs configuring the user interface window.

The storage 220 may store a variety of programs and data which are required to operate the user terminal device 200. Specifically, the storage 220 may store the program, the data, and the like for configuring a variety of UIs configuring the user interface window.

In addition, the storage 220 stores a variety of contents. Here, the contents may be a pattern of the selected exercise received from the external device. Meanwhile, the contents may be a plurality of exercise patterns, an image corresponding to each of the exercise patterns, and an image of a right exercise posture.

In addition, the storage 220 may store at least one of the motion information received from the external device and the motion pattern extracted based on the motion pattern. In addition, the storage 220 may compare the pattern of the selected exercise with the extracted motion pattern and store the counted number of times of execution of the exercise.

In addition, the storage 220 may store the biological signals of the user received from the external device and the exercise effect information calculated based on the measured biological signals.

The user interface 230 may display a plurality of exercises and may be selected with one of the plurality of displayed exercises. Specifically, the user interface 230 may be a touch screen that displays the plurality of exercises and may receive the selection of the user, or a button, a wheel, a dial, or the like that may select one of the plurality of exercises, when the plurality of exercises are displayed on a separate display included in the user terminal device 200. Hereinafter, the user interface 230 according to the present disclosure will be illustrated and described as being limited to the touch screen.

In this case, an example of a user interface window which may be displayed will be described below wither reference to FIG. 7. Meanwhile, if the touch screen 230 is selected with one exercise, the touch screen 230 may display a right execution posture of the selected exercise. In this case, the touch screen 230 may display the right execution posture of the selected exercise in the form of GIF, AVI, JPG, and JPEG.

Meanwhile, the user interface 230 may display at least one of a time limit and a target number of times to perform exercise together with the right execution posture of the selected exercise. In this case, after the touch screen 230 displays at least one of the right execution posture, the time limit, and the target number of times of the selected exercise, if there is a touch of the user or a predetermined time has elapsed, the touch screen 230 may display at least one of the remaining time of the time limit and the counted number of times of execution.

Meanwhile, if the exercise of the user is completed, the user interface 230 may display the counted number of times of execution and the number of times that the exercise is performed in a right posture. In this case, the user interface 230 may further display the calculated exercise effect such as an amount of calorie consumption, a change in body temperature, a change in heartbeat, a change in skin resistance, and the like. In this case, an example of a user interface window which may be displayed will be described below in detail with reference to FIG. 13. Meanwhile, hereinabove, although the user interface 230 is described as being limited to the touch screen, the user interface 230 may also be implemented by a scheme of providing the counted number of times of execution to the user using the LED or the like included in the user terminal device 200 at the time of implementation.

The processor 240 may display the user interface window on the user interface 230 using the programs and the data stored in the storage 220. In addition, if the user touches a specific region of the user interface window, the processor 240 may perform a control operation corresponding to the touch. Specifically, the processor 240 may control the interface 230 to display the plurality of exercises and to be selected with one of the plurality of displayed exercises. In this case, if the user selects one exercise, the processor 240 may control the user interface 230 to display the right posture of the selected exercise and display a time limit and a target number of times together with the right posture.

Meanwhile, the processor 240 may control the communicator 210 to receive at least one of the motion information and the biological signals sensed by the wearable device. In this case, the processor 240 may control the communicator 210 to receive the number of times that the preselected exercise is performed counted by the external device and the exercise effect information from the external device.

Meanwhile, the processor 240 may control the communicator 210 to receive information on the preselected exercise from the external device. In this case, the exercise information may include at least one of exercise selected by the user in the external device and an exercise pattern corresponding to the exercise selected by the user.

Meanwhile, if the wearable device including the NFC module is tagged with the external device on which the NFC tag is mounted, the processor 240 may control the communicator 210 to receive information corresponding to the tagged external device from the external device. For example, if the wearable device including the NFC module is tagged with a health instrument on which the NFC tag is mounted, the processor 240 may control the communicator 210 to receive information corresponding to the tagged health instrument from the server. In this case, the information corresponding to the health instrument may be selection information of the user when exercise patterns of a plurality of health instruments are stored in the user terminal device 200, and may be an exercise pattern of the tagged health instrument when the exercise patterns of the plurality of health instruments are not stored in the user terminal device 200.

Meanwhile, the processor 240 may extract the motion pattern of the wearable device received from the external device. In this case, the processor 240 may compare the extracted motion pattern with a pattern of the preselected exercise, and count the number of times that the user performs exercise corresponding to the corresponding exercise pattern. In this case, the processor 240 may compare the extracted motion pattern with the pattern of the preselected exercise, and determine an accuracy of the exercise performed by the user. Specifically, the processor 240 may compare the extracted motion pattern with the pattern of the preselected exercise, and count the number of times that the user performs the exercise in the right posture. Meanwhile, a criterion for determining whether or not the user performs the exercise in the right posture will be described below with reference to FIGS. 11 and 12.

In this case, the processor 240 may update the prestored exercise pattern according to the determined posture that the user performs the exercise. Specifically, the processor 240 may compare the exercise pattern stored in the database with the extracted motion pattern of the user, and determine whether or not the user performs the exercise in the right posture. In this case, if a difference between the motion pattern and the exercise pattern of the user corresponds to a predetermined range, and the counted number of times corresponds to a predetermined value or more when the number of times corresponding to the predetermined range is counted, the processor 240 may update the prestored exercise pattern to suit the user.

Meanwhile, a method for updating the prestored exercise pattern will be described below in detail with reference to FIG. 24.

Meanwhile, the processor 240 may calculate the exercise effect such as an amount of calorie consumption, a change in body temperature, a change in heartbeat, and a change in skin resistance using at least one of heartbeat, body temperature, and skin resistance which are measured before and after the exercise received from the external device.

Meanwhile, the processor 240 may control the user interface 230 to display the calculated exercise result. Specifically, the processor 240 may control the user interface 230 to display the exercise effect such as the number of times that the user performs the exercise, the number of times that the user performs the exercise in the right posture, the amount of calorie consumption, and the like. In this case, an example of a user interface window which may be displayed will be described below in detail with reference to FIG. 13.

Meanwhile, the processor 240 may compare a time limit and the target number of times which are present before the user begins the exercise with the number of times that the user performs the exercise to modify the target number of times stored in the storage 220. For example, if the user completes the target number of times within the presented time limit, the processor 240 may increase the target number of times or reduce the time limit and may store the increased target number of times or the reduced time limit. Thereby, the user terminal device 200 may present exercise of the adjusted intensity according to exercise ability of the user. Meanwhile, a method for modifying the exercise intensity according to the counted number of times that the exercise is performed will be described below in detail with reference to FIGS. 21 and 22.

Figure 6:
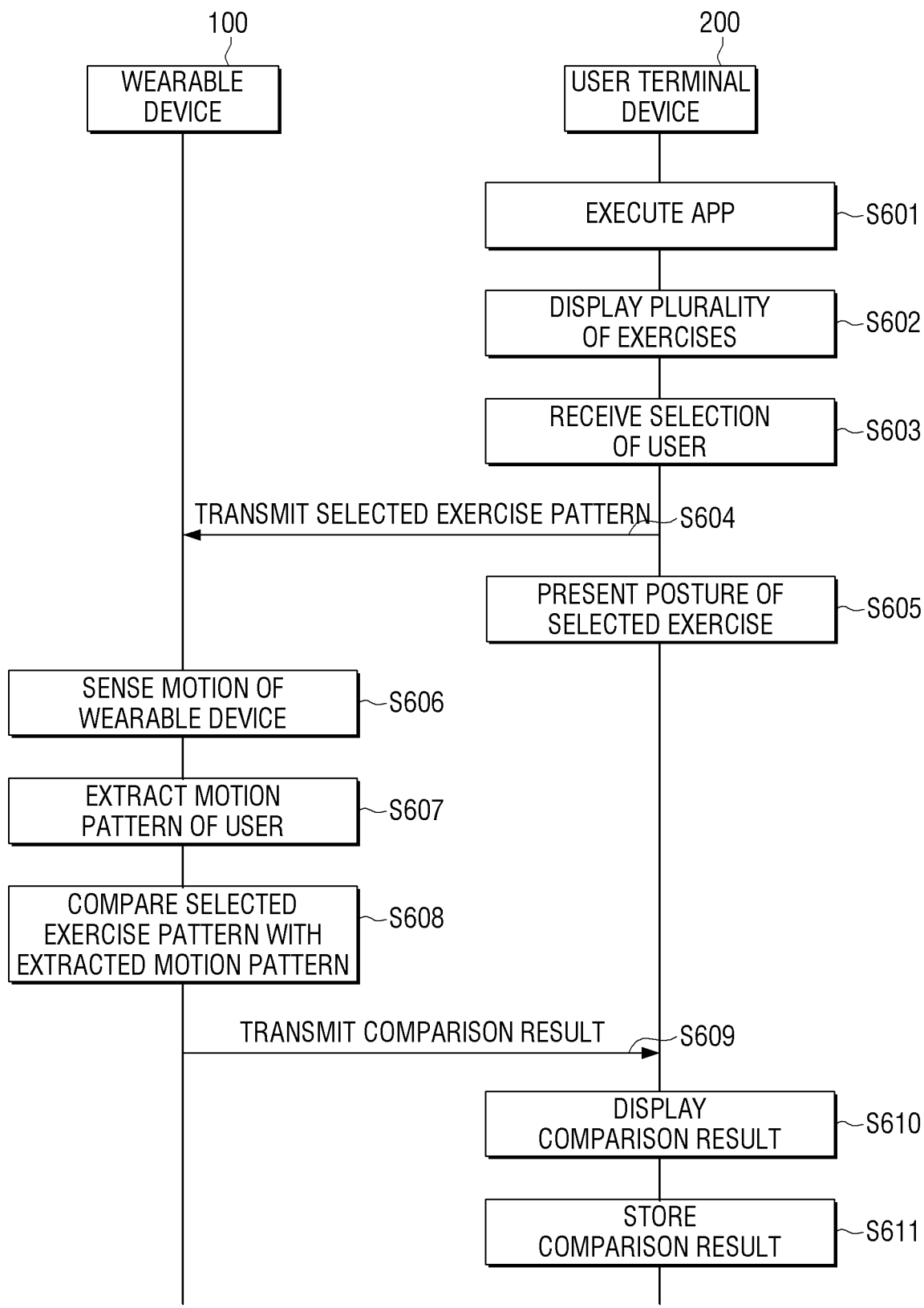
FIGS. 6 and 14 are flowcharts illustrating processes of measuring an exercise result to manage exercise of a user according to diverse exemplary embodiments of the present disclosure.

FIG. 6 is a flowchart illustrating a process of measuring an exercise result to manage exercise of a user according to an exemplary embodiment of the present disclosure.

Referring to FIG. 6, first, the user executes an exercise management application (hereinafter, referred to app) in the user terminal device 200 (S601). Next, the user terminal device 200 displays a plurality of exercises (S602). In this case, the plurality of displayed exercises may be those stored in the user terminal device 200, or those received from the external device.

Next, the user terminal device 200 receives a selection of the user (S603). In this case, the user may select one exercise of the plurality of displayed exercises. In this case, the user terminal device 200 may limit an exercise pattern to be compared with a motion pattern of the user among a plurality of stored exercise patterns, by the selection of the user. A method for limiting one exercise pattern of the plurality of exercise patterns will be described below in detail with reference to FIGS. 7 and 8.

Hereinabove, although the method for selecting one exercise of the plurality of exercises by the user is described as being limited to selecting one exercise using the user terminal device 200, at the time of actual implementation, if the wearable device 100 includes a display, a method for limiting the exercise pattern to be compared with the motion pattern of the user by selecting the exercise in the same method may be implemented even in the wearable device 100.

Next, the user terminal device 200 transmits an exercise pattern corresponding to the selected exercise to the wearable device 100 (S604).

Next, the user terminal device 200 presents a right posture corresponding to the selected exercise (S605). Specifically, the user terminal device 200 may display the right posture corresponding to the selected exercise through the user interface. Meanwhile, for convenience of explanation, although the user terminal device 200 is illustrated and described to present a posture of the selected exercise after transmitting the exercise pattern of the selected exercise to the wearable device 100, the order may be arbitrary at the time of actual implementation.

Next, the wearable device 100 may present the posture of the exercise selected in the user terminal device 200 and then sense a motion of the wearable device 100 (S606). Specifically, the wearable device 100 may sense the motion of the wearable device 100 using a sensor included therein. In this case, if the wearable device 100 presents the right posture of the exercise selected in the user terminal device 200 and a predetermined event then occurs, the wearable device 100 may measure the motion of the wearable device 100. In this case, the predetermined event may be a case in which a predetermined time has lapsed after presenting the posture, or the user performs an input or a touch using the user interface of the wearable device 100 or the user terminal device 200.

Next, the user terminal device 200 may extract a motion pattern of the user wearing the wearable device 100 based on the sensed motion information of the wearable device 100 (S607).

Next, the wearable device 100 may compare the selected exercise pattern with the extracted motion pattern (S608). In this case, the selected exercise pattern may be an exercise pattern received from the user terminal device 200. Meanwhile, the selected exercise pattern may be an exercise pattern corresponding to the exercise selected through the user interface included in the wearable device 100. In this case, the user terminal device 200 may compare the selected exercise pattern with the extracted motion pattern, and count the number of times that the user performs the exercise. Meanwhile, a method for comparing the selected exercise pattern with the extracted motion pattern and counting the number of times that the user performs the exercise will be described below in detail with reference to FIG. 10.

Next, the wearable device 100 may transmit the comparison result to the user terminal device 200 (S609). In this case, the comparison result may be the number of times that the user performs the exercise counted by comparing the selected exercise pattern with the extracted motion pattern. Meanwhile, the comparison result may be exercise effect information calculated based on biological signals of the user measured through a body contact sensor included in the wearable device 100. An exemplary embodiment in which the exercise effect information is included in the comparison result will be described below in detail with reference to FIG. 21.

Next, the user terminal device 200 receiving the comparison result from the wearable device 100 may display the received comparison result on the user interface included in the user terminal device 200 (S610). Meanwhile, for convenience of explanation, although the comparison result is illustrated and described as being transmitted to the user terminal device 200 and displayed thereon, at the time of actual implementation, when the wearable deice 100 includes a display as the user interface, the comparison result may be displayed on the display of the wearable device 100. Meanwhile, when the wearable device 100 includes an LED, the result may be displayed by displaying the LED as many times as the counted number of times.

Next, the user terminal device 200 may store the received comparison result (S611). Meanwhile, for convenience of explanation, although the comparison result is illustrated and described as being stored in the user terminal device 200, at the time of actual implementation, the comparison result may be stored in the wearable device 100, and may also be implemented in the form in which it is transmitted to the server, which is the external device, and stored therein. Meanwhile, an exemplary embodiment using the server will be described below in detail with reference to FIGS. 14 to 19. As described above, the number of times that the preselected exercise is performed is counted and recorded using the wearable device 100, thereby making it possible to more conveniently manage the exercise of the user.

Figure 8:
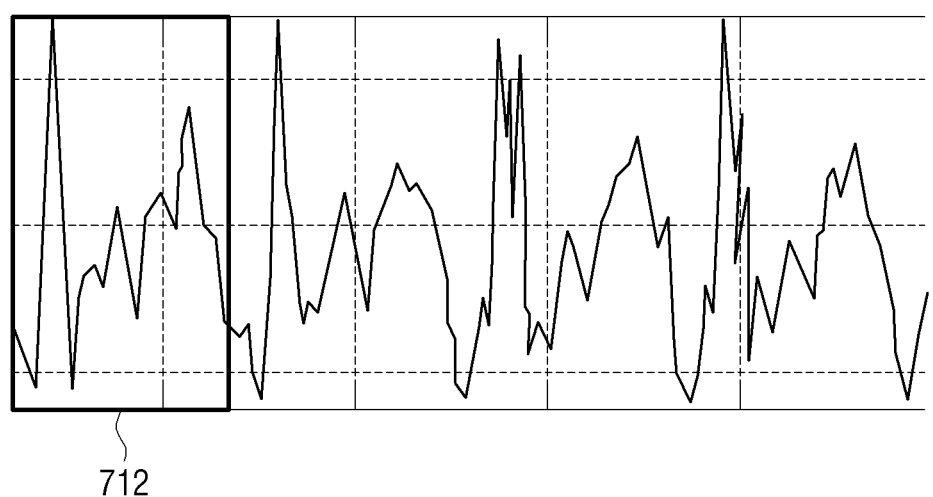

FIGS. 7 and 8 are diagrams illustrating a method for limiting an exercise pattern to be compared with a measured motion of the user.

Referring to FIG. 7A, a user 10 may select one of a plurality of exercises displayed on the user interface 230 of the user terminal device 200. For example, the plurality of exercises may include a P.T jump 710, a squat 720, a sit-up, a leg lift jump, a lunge, and the like. In this case, the user 10 may select the P.T jump 710 among the plurality of exercises.

In this case, the user terminal device 200 may limit a pattern corresponding to the exercise selected by the user to the exercise pattern information to be compared with the motion of the user. In this case, the exercise pattern information is stored in the database which is measured and stored for each of the exercises in advance, and may mean that when the user wears the wearable device and continuously repeats the same exercise, the same motion is repeatedly sensed in the wearable device.

Referring to FIG. 7B, the user terminal device 200 may limit the pattern information corresponding to the exercise selected by the user 10 among the plurality of exercise pattern information to a pattern to be compared with the motion of the user. For example, the user terminal device 200 may limit exercise pattern information 711 corresponding to the P.T jump 710 according to the selection of the user 10 selecting the P.T jump 710 among the exercise pattern information 711 corresponding to the P.T jump 710 and exercise pattern information 721 corresponding to the squat 720 which are stored to the exercise pattern information to be compared with the motion of the user. Meanwhile, the exercise pattern information illustrated in FIG. 7B is merely illustrated for convenience of explanation, and may also not be displayed on the user interface at the time of actual implementation.

Referring to FIG. 8, the user terminal device 200 may extract the exercise pattern 712 to be compared with the motion pattern of the user from the exercise pattern information 711 of the P.T jump limited by the selection of the user. Specifically, the user terminal device 200 may extract one pattern among the same repeated patterns of the pre-stored exercise pattern information as the exercise pattern 712 to be compared with the motion pattern of the user.

Meanwhile, although FIGS. 7 and 8 illustrate and describe that one exercise of the plurality of exercises is selected by the user 10 from the user terminal device 200 and the exercise pattern to be compared with the motion of the user is limited, at the time of actual implementation, one exercise of the plurality of exercises may be selected by the user from the wearable device including the display as the user interface, or the exercise pattern to be compared with the motion of the user may be limited through the NFC tag between the wearable device and the external device.

Figure 9:
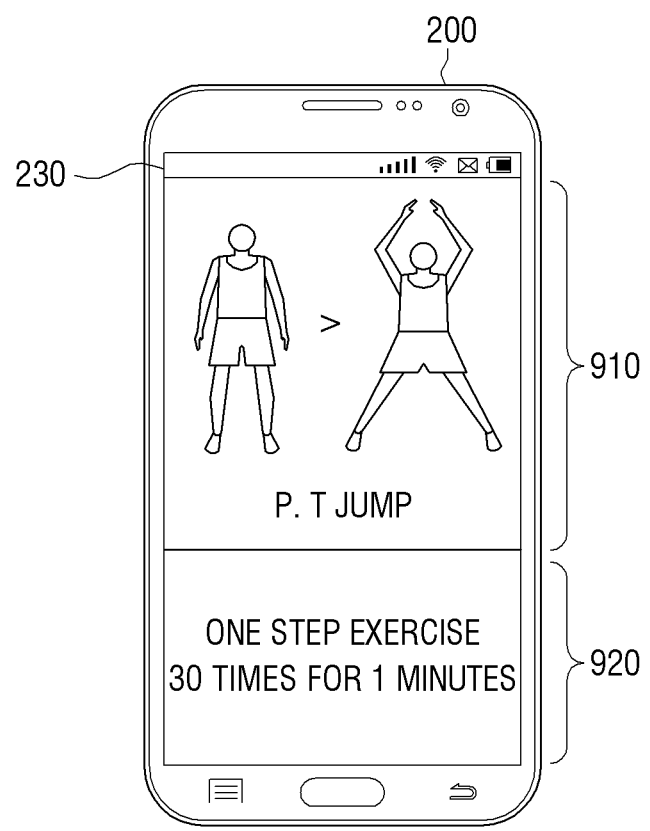
FIG. 9 is a diagram illustrating a method for presenting right exercise posture and exercise intensity to manage exercise of a user according to an exemplary embodiment of the present disclosure.

FIG. 9 is a diagram illustrating a method for presenting right exercise posture and exercise intensity to manage exercise of a user according to an exemplary embodiment of the present disclosure.

Referring to FIG. 9, if the user selects one exercise of the plurality of exercises, the user terminal device 200 may present a right posture of the selected exercise. Specifically, if the user selects one exercise of the plurality of exercises, the user interface 230 included in the user terminal device 200 may display a right posture 910 of the selected exercise. Specifically, the user interface 230 may present the right posture of the selected exercise using a plurality of images. Meanwhile, the presentation of the right posture is not limited thereto, and the user interface 230 may present the right posture of the selected exercise using videos such as GIF, AVI, and the like. Meanwhile, the user terminal device 200 may provide voice information on a detailed operation while displaying the right posture 910 of the exercise selected by the user.

Meanwhile, the user terminal device 200 may present appropriate exercise intensity together with the right posture 910 of the selected exercise. Specifically, the user interface 230 included in the user terminal device 200 may display a time limit and the target number of times 920 together with the right posture 910 of the selected exercise.

In this case, the exercise intensity including the time limit and the target number of times may be prestored, and the stored exercise intensity may be then modified and stored by determining the number of times that the user performs the exercise and an accuracy of the exercise performed by the user. Specifically, if the user completes the target number of times within the presented time limit, the user terminal device 200 may reduce the time limit by increasing the exercise intensity or increase and store the target number of times. Thereafter, if the user selects the same exercise, the user terminal device 200 may present the increased exercise intensity. A method for updating the exercise intensity according to the measured exercise result of the user will be described below in detail with reference to FIG. 21.

Meanwhile, for convenience of explanation, although the present disclosure is illustrated and described as being limited to the case in which the user terminal device 200 presents the right posture and the exercise intensity of the selected exercise if the user selects one exercise of the plurality of exercises, but the right posture and the exercise intensity of the selected exercise may be presented using the wearable device including the touch screen as the user interface.

Figure 10:
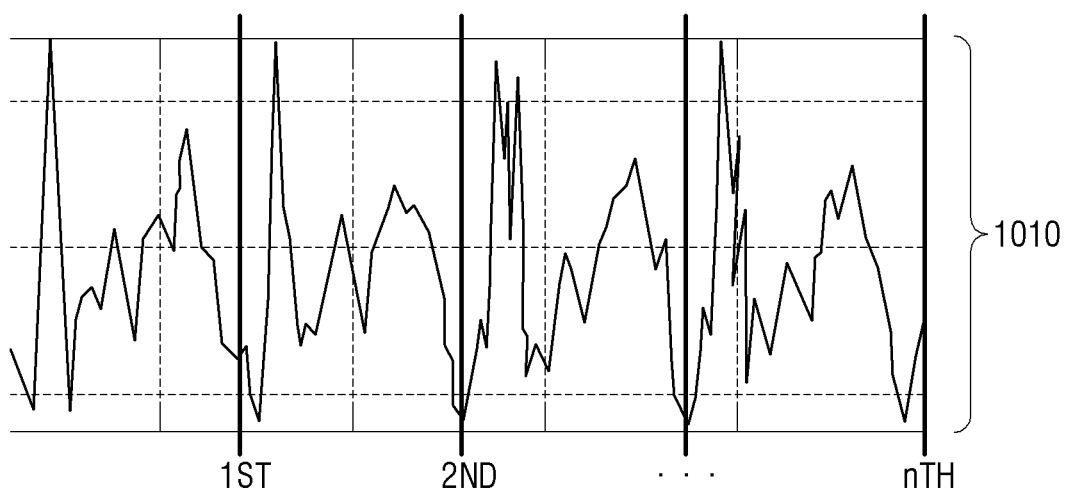
FIG. 10 is a diagram illustrating a method for measuring the number of times of exercise of a user according to an exemplary embodiment of the present disclosure.

FIG. 10 is a diagram illustrating a method for measuring the number of times of exercise of a user according to an exemplary embodiment of the present disclosure.

FIG. 10 illustrates motion pattern information 1010 of the user extracted based on the motion sensed by the wearing device worn by the user while the user performs preselected exercise. In this case, the wearable device may compare the exercise pattern of the preselected exercise limited in FIG. 8 with the sensed and extracted motion pattern information 1010 of the user and count the number of times that the user performs the preselected exercise. Specifically, the wearable device may count the number of times that the user performs the preselected exercise by counting the number of times that an exercise pattern of the preselected exercise is repeated in the extracted motion pattern information 1010 of the user.

Meanwhile, hereinabove, for convenience of explanation, although the present disclosure is described as being limited to the case in which the wearable device counts the number of times that the user performs the preselected exercise, at the time of actual implementation, the number of times that the user performs the preselected exercise may be counted by the external device such as the user terminal device, the server, or the like. This will be described below in detail with reference to FIGS. 14 and 18.

FIG. 11 is a diagram illustrating a method for determining an exercise posture of a user according to an exemplary embodiment of the present disclosure.

Referring to FIG. 11, the wearable device may compare the extracted exercise pattern information of the user with the preselected exercise pattern and determine the accuracy of the exercise performed by the user. For example, the wearable device may compare the extracted exercise pattern information of the user with the preselected exercise pattern and determine the accuracy that the exercise performed by the user corresponds to any one of a good performing posture (Good), a normal performing posture (Normal), and a bad performing posture (Bad). Specifically, the wearable device may determine the good performing posture (Good) when the exercise performed by the user completes the presented posture within a time limit, may determine the normal performing posture (Normal) when a noise pattern appears in the extracted exercise pattern information of the user or it takes to more time than the time limit to perform the presented target number of times, and may determine the bad performing posture (Bad) when a pattern included in the extracted exercise pattern information of the user is completely different from the preselected exercise pattern.

Meanwhile, for convenience of explanation, although the accuracy of the exercise performed by the user is illustrated and described as being limited to be determined by dividing into three steps, the accuracy of the exercise performed by the user may be variously implemented in two steps or less, or four steps or more.

Meanwhile, hereinabove, for convenience of explanation, although the present disclosure is described as being limited to the case in which the wearable device determines the accuracy of the preselected exercise performed by the user, at the time of actual implementation, the accuracy of the preselected exercise performed by the user may be determined by the external device such as the user terminal device, the server, or the like.

Figure 12:
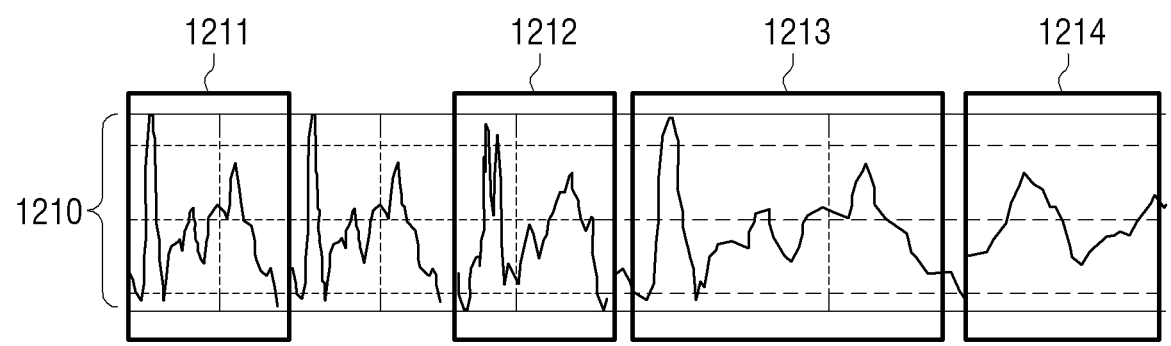
FIG. 12 is a diagram illustrating diverse examples determining the exercise posture of the user according to FIG. 11.

FIG. 12 is a diagram illustrating diverse examples determining the exercise posture of the user according to FIG. 11.

FIG. 12 illustrates motion pattern information 1210 of the user extracted based on the motion sensed by the wearing device worn by the user while the user performs preselected exercise.

In this case, the wearable device may compare the exercise pattern 712 of the preselected exercise illustrated in FIG. 8 with the extracted motion pattern information 1210 of the user and count the accuracy of the preselected exercise performed by the user. For example, since a first pattern 1211 of the extracted motion pattern information 1210 of the user is very similar to the exercise pattern 712 of the preselected exercise, the wearable device may determine that an operation corresponding to the first pattern 1211 performed by the user is the good performing posture. Meanwhile, since a third pattern 1212 of the extracted motion pattern information 1210 of the user includes the noise pattern as compared to the exercise pattern 712 of the preselected exercise, the wearable device may determine that an operation corresponding to the third pattern 1212 performed by the user is the normal performing posture. Meanwhile, since a fourth pattern 1213 of the extracted motion pattern information 1210 of the user shows that an operation is performed over the time limit as compared to the exercise pattern 712 of the preselected exercise, the wearable device may determine that an operation corresponding to the fourth pattern 1213 performed by the user is the normal performing posture. Meanwhile, since a fifth pattern 1214 of the extracted motion pattern information 1210 of the user is completely different from the exercise pattern 712 of the preselected exercise, the wearable device may determine that an operation corresponding to the fifth pattern 1214 performed by the user is the bad performing posture.

Meanwhile, hereinabove, for convenience of explanation, although the present disclosure is described as being limited to the case in which the wearable device determines the accuracy of the preselected exercise performed by the user, at the time of actual implementation, the accuracy of the preselected exercise performed by the user may be determined by the external device such as the user terminal device, the server, or the like.

Meanwhile, since the method for determining the accuracy of the exercise described above is merely one example, the accuracy of the exercise may be implemented by various criteria such as a setting of the user, a setting of a device manufacturer, and the like at the time of actual implementation.

Figure 13:
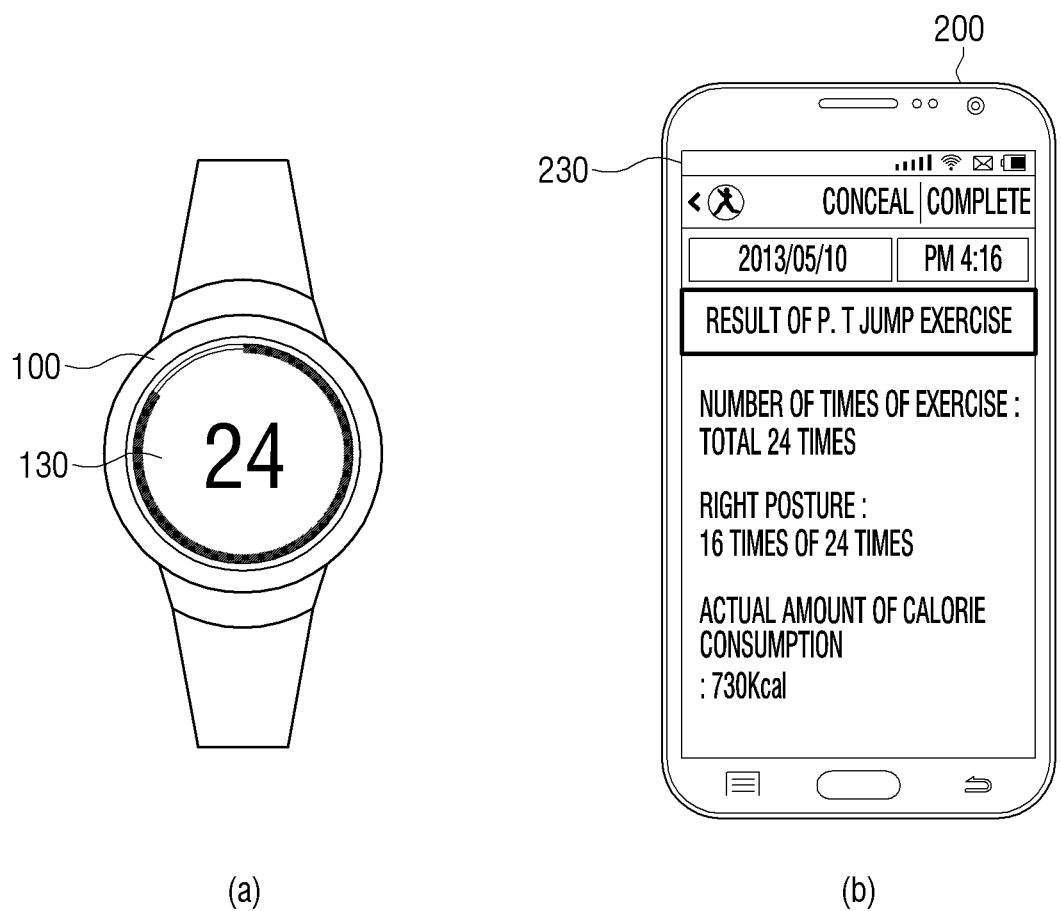
FIGS. 13 and 20 are diagrams illustrating examples providing a measured exercise result to the user according to an exemplary embodiment of the present disclosure.

FIG. 13 is a diagram illustrating an example providing a measured exercise result to the user according to an exemplary embodiment of the present disclosure. Specifically, FIG. 13A is a diagram illustrating an example providing the measured exercise result to the wearable device 100 worn by the user while the user performs the exercise and FIG. 13B is a diagram illustrating an example providing the measured exercise result to the user terminal device 200 connectable to the wearable device 100.

Referring to FIG. 13A, the user interface 130 included in the wearable device 100 may display the number of times that the user performs the preselected exercise. Specifically, the user interface 130 included in the wearable device 100 may display the number of times that the user performs the preselected exercise as a count value. In this case, the number of times may be the number of times counted by the wearable device and may be the number of times counted and received from the external device.

Referring to FIG. 13B, the user interface 130 included in the user terminal device 200 may display at least one of the number of times that the user performs the preselected exercise, the accuracy of the exercise performed by the user, and the exercise effect information such as the amount of calorie consumption. In this case, the number of times that the user performs the preselected exercise, the accuracy, and the exercise effect information which are displayed may be those received from the wearable device 100, or those calculated by the user terminal device 200.

Meanwhile, for convenience of explanation, although the present disclosure is illustrated and described as being limited to the case in which only the number of times that the user performs the preselected exercise is displayed on the user interface 130 included in the wearable device 100, at the time of actual implementation, the present disclosure is not limited thereto, and as illustrated in FIG. 13B, the accuracy of the exercise performed by the user or the exercise effect information may also be displayed together.

Figure 14:
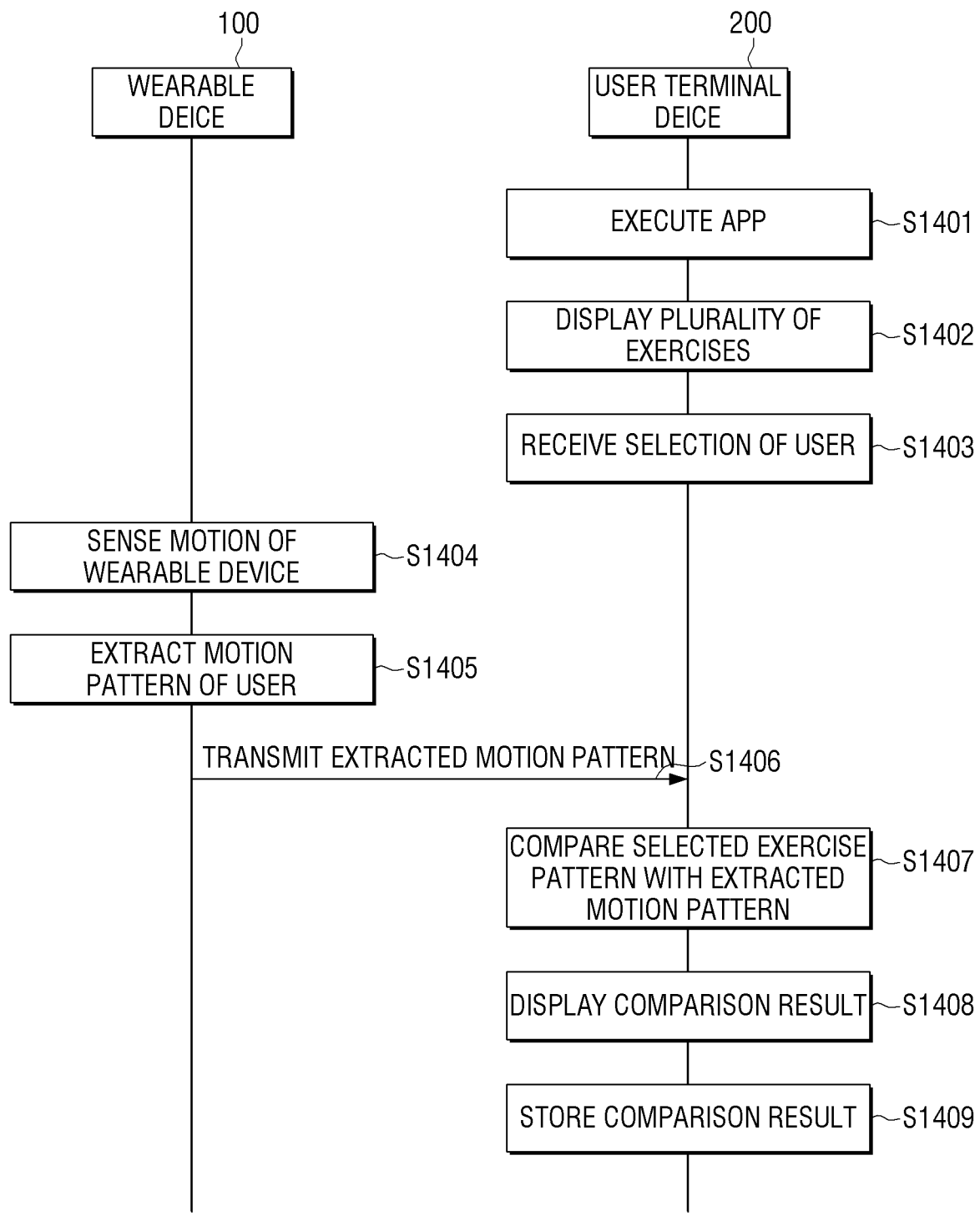

FIG. 14 is a flowchart illustrating a process of measuring an exercise result to manage exercise of a user according to an exemplary embodiment of the present disclosure.

Referring to FIG. 14, first, the user executes an exercise management application (hereinafter, referred to app) in the user terminal device 200 (S1401). Next, the user terminal device 200 displays a plurality of exercises (S1402). In this case, the plurality of displayed exercises may be those stored in the user terminal device 200, or those received from the external device.

Next, the user terminal device 200 receives a selection of the user (S1403). In this case, the user may select one exercise of the plurality of displayed exercises. In this case, the user terminal device 200 may limit an exercise pattern to be compared with a motion pattern of the user among a plurality of stored exercise patterns, by the selection of the user. A method for limiting one exercise pattern of the plurality of exercise patterns refers to FIGS. 7 and 8.

Hereinabove, although the method for selecting one exercise of the plurality of exercises by the user is described as being limited to selecting one exercise using the user terminal device 200, at the time of actual implementation, if the wearable device 100 includes a display, a method for limiting the exercise pattern to be compared with the motion pattern of the user by selecting the exercise in the same method may be implemented even in the wearable device 100.

In this case, although not illustrated, if the user selects one exercise, the user terminal device 200 may present a right posture corresponding to the selected exercise. Specifically, the user terminal device 200 may display the right posture corresponding to the selected exercise through the user interface. In this case, the user terminal device 200 may display a time limit and the target number of times in which the exercise is to be performed, together with the right posture corresponding to the selected exercise.

Next, the wearable device 100 may present the posture of the exercise selected in the user terminal device 200 and then sense a motion of the wearable device 100 (S1404). Specifically, the wearable device 100 may sense the motion of the wearable device 100 using a sensor included therein. In this case, if the wearable device 100 presents the right posture of the exercise selected in the user terminal device 200 and a predetermined event then occurs, the wearable device 100 may measure the motion of the wearable device 100. In this case, the predetermined event may be a case in which a predetermined time has lapsed after presenting the posture, or the user performs an input or a touch using the user interface of the wearable device 100 or the user terminal device 200.

Next, the wearable device 100 may extract motion pattern information of the user wearing the wearable device 100 based on the sensed motion information of the wearable device 100 (S1405).

Next, the wearable device 100 may transmit the extracted motion pattern information of the user to the user terminal device 200 (S1406). For convenience of explanation, although the present disclosure is illustrated and described as being limited to the case in which the motion pattern information of the user is extracted from the wearable device 100 and is transmitted to the user terminal device 200, at the time of actual implementation, the present disclosure may be implemented in the form in which the wearable device 100 transmits only the sensed motion information of the wearable device 100 to the user terminal device 200 and extracts the motion pattern information of the user based on the motion information of the wearable device 100 received by the user terminal device 200.

Next, the user terminal device 200 may compare the selected exercise pattern with the extracted motion pattern (S1407). In this case, the selected exercise pattern may be an exercise pattern corresponding to the exercise selected in the user terminal device 200. Meanwhile, the selected exercise pattern may be an exercise pattern corresponding to the exercise selected through the user interface included in the wearable device 100. In this case, the user terminal device 200 may compare the selected exercise pattern with the extracted motion pattern, and count the number of times that the user performs the exercise. Meanwhile, a method for comparing the selected exercise pattern with the extracted motion pattern and counting the number of times that the user performs the exercise refers to FIG. 10.

Next, the user terminal device 200 may display the comparison result on the user interface included therein (S1408).

Next, the user terminal device 200 may store the comparison result (S1409). Meanwhile, for convenience of explanation, although the comparison result is illustrated and described as being stored in the user terminal device 200, at the time of actual implementation, the comparison result may be stored in the wearable device 100, and may also be implemented in the form in which it is transmitted to the server, which is the external device, and stored therein. Meanwhile, an exemplary embodiment using the server will be described below in detail with reference to FIGS. 14 to 19. As described above, since the information sensed and measured by the wearable device 100 is immediately transmitted to the user terminal device 200 and the information received by the user terminal device 200 is processed, the exercise management system according to the present disclosure may be implemented even in a case in which the wearable device 100 does not include a large capacity battery and a large capacity memory.

Figure 15:
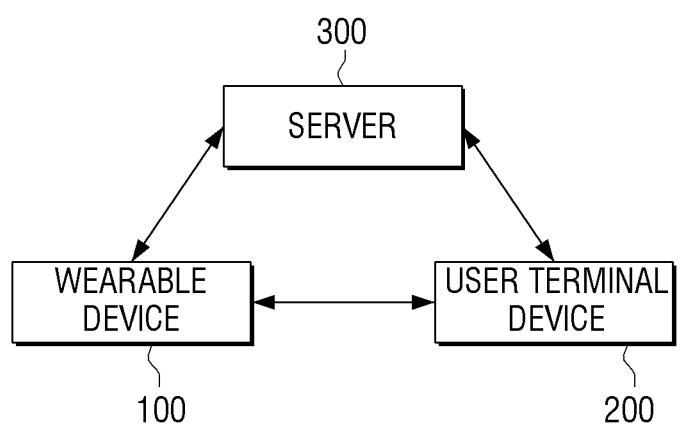
FIG. 15 is a drawing illustrating a configuration of an exercise management system of a user that further uses a server according to an exemplary embodiment of the present disclosure.

FIG. 15 is a drawing illustrating a configuration of an exercise management system of a user that further uses a server according to an exemplary embodiment of the present disclosure.

Referring to FIG. 15, the exercise management system of the user according to an exemplary embodiment of the present disclosure includes the wearable device 100, the user terminal device 200, and a server 300.

Since the wearable device 100 and the user terminal device 200 included in the exercise management system of the user according to an exemplary embodiment of the present disclosure are the same components as the components illustrated in FIG. 1, a detailed description thereof will be omitted.

The server 300 may interact with at least one of the wearable device 100 and the user terminal device 200. Specifically, the server 300 may receive at least one of exercise information selected by the user and measured information from at least one of the wearable device 100 and the user terminal device 200. In this case, the server 300 may transmit an exercise pattern corresponding to the exercise information selected by the user among a plurality of prestored exercise patterns to at least one of the wearable device 100 and the user terminal device 200. Meanwhile, the server 300 may count the number of times that the user performs the preselected exercise based on the received information and calculate the exercise effect to transmit them to at least one of the wearable device 100 and the user terminal device 200.

Meanwhile, a detailed configuration and operation of the server 300 will be described below in detail with reference to FIG. 16.

Figure 16:
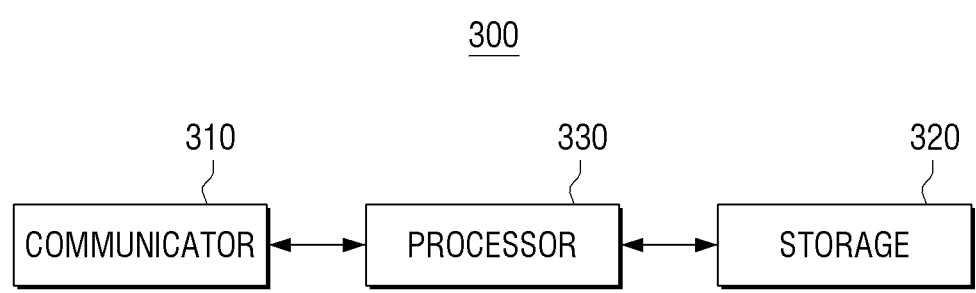
FIG. 16 is a block diagram illustrating a configuration of a server according to an exemplary embodiment of the present disclosure.

FIG. 16 is a block diagram illustrating a configuration of a server according to an exemplary embodiment of the present disclosure.

Referring to FIG. 16, the server 300 may include a communicator 210, a storage 320, and a processor 330.

The communicator 310 may be formed to connect the server 300 to the external device, and may connect the server 300 to the external device via a local area network (LAN) and an Internet network and may also connect the server 300 to the external device via a universal serial bus (USB) port and a wireless module. Here, the wireless module may be WiFi, WiFi Direct, near field communication (NFC), Bluetooth, or the like.

Meanwhile, the communicator 310 may receive the exercise information selected by the user from the wearable device and the user terminal device. In this case, the exercise information may include at least one of exercise selected by the user in the wearable device or the user terminal device and an exercise pattern corresponding to the exercise selected by the user. In addition, the communicator 310 may transmit an exercise pattern corresponding to the exercise selected by the user to the wearable device and the user terminal device according to the received exercise information.

Meanwhile, the communicator 310 may receive at least one of motion information of the wearable device sensed in the wearable device and the number of times that the user performs the preselected exercise counted based on the motion information of the wearable device. In addition, communicator 310 may receive the measured biological signals and the calculated exercise effect information from the wearable device. Specifically, the communicator 310 may receive at least one of at least one biological information among heartbeat, body temperature, and skin resistance of the user which are measured in the wearable device, and the exercise effect information calculated based on the measured biological information, together with at least one of the motion information of the wearable device and the counted number of times that the user performs the preselected exercise.

Meanwhile, the communicator 310 may transmit a result obtained by comparing the preselected exercise pattern with the extracted motion pattern of the user to at least one of the wearable device and the user terminal device to provide the comparison result to the user.

The storage 320 may store exercise patterns corresponding to a plurality of exercises. In addition, the storage 320 may store the result obtained by comparing the preselected exercise pattern with the extracted motion pattern of the user. In this case, the storage 320 may further store the exercise effect information calculated based on the measured biological signals of the user.

The processor 330 may control the communicator 310 to receive the exercise information selected by the user from the wearable device and the user terminal device and to transmit exercise information corresponding to the preselected exercise among the plurality of stored exercise patterns to the wearable device and the user terminal device.

In addition, the processor 330 may receive the exercise information selected by the user from the wearable device and the user terminal device to limit the exercise pattern corresponding to the preselected exercise among the plurality of stored exercise patterns.

Meanwhile, the processor 330 may control the communicator 310 to receive at least one of the sensed motion information of the wearable device and the motion pattern information of the user extracted based on the motion information of the wearable device from the wearable device. In this case, in a case in which the sensed motion information of the wearable device is received from the wearable device, the processor 330 may extract the motion pattern information of the user from the received motion information. In this case, the processor 330 may control the communicator 310 to further receive the measured biological signals of the user from the wearable device, together with at least one of the motion information of the wearable device and the motion pattern information of the user extracted based on the motion information of the wearable device.

Meanwhile, the processor 330 may compare a limited exercise pattern with the motion pattern information of the user and count the number of time that the user performs the preselected exercise. In this case, a method for counting the number of times that the user performs the preselected exercise refers to FIG. 10.

Meanwhile, the processor 330 may compare the limited exercise pattern with the motion pattern information of the user and determine an accuracy of the preselected exercise performed by the user. In this case, a method for determining the accuracy of the exercise performed by the user refers to FIGS. 11 and 12.

Meanwhile, the processor 300 may modify and store exercise intensity presented to the user and the prestored exercise pattern according to the counted number of times that the user performs the preselected exercise and the determined posture in which the user performs the exercise. Specifically, if the user completes the presented target number of times within the presented time limit, the processor 330 may reduce the time limit or increase the target number of times and may store the reduced time limit or the increased target number of times. Thereby, when the user selects the same exercise later, the increased exercise intensity is presented, thereby making it possible to allow the user to effectively perform the exercise.

Meanwhile, the processor 330 may calculate the exercise effect of the user based on the received biological signals of the user. Specifically, the processor 330 may calculate the exercise effect such as a change in heartbeat, a change in body temperature, and a change in skin resistance, and an amount of calorie consumption by receiving at least one information of heartbeat, body temperature, and skin resistance which are measured before and after the exercise.

Meanwhile, the processor 330 may control the communicator 310 to transmit at least one of the counted number of times and the calculated exercise effect to the wearable device and the user terminal device and to provide it to the user.

Figure 17:
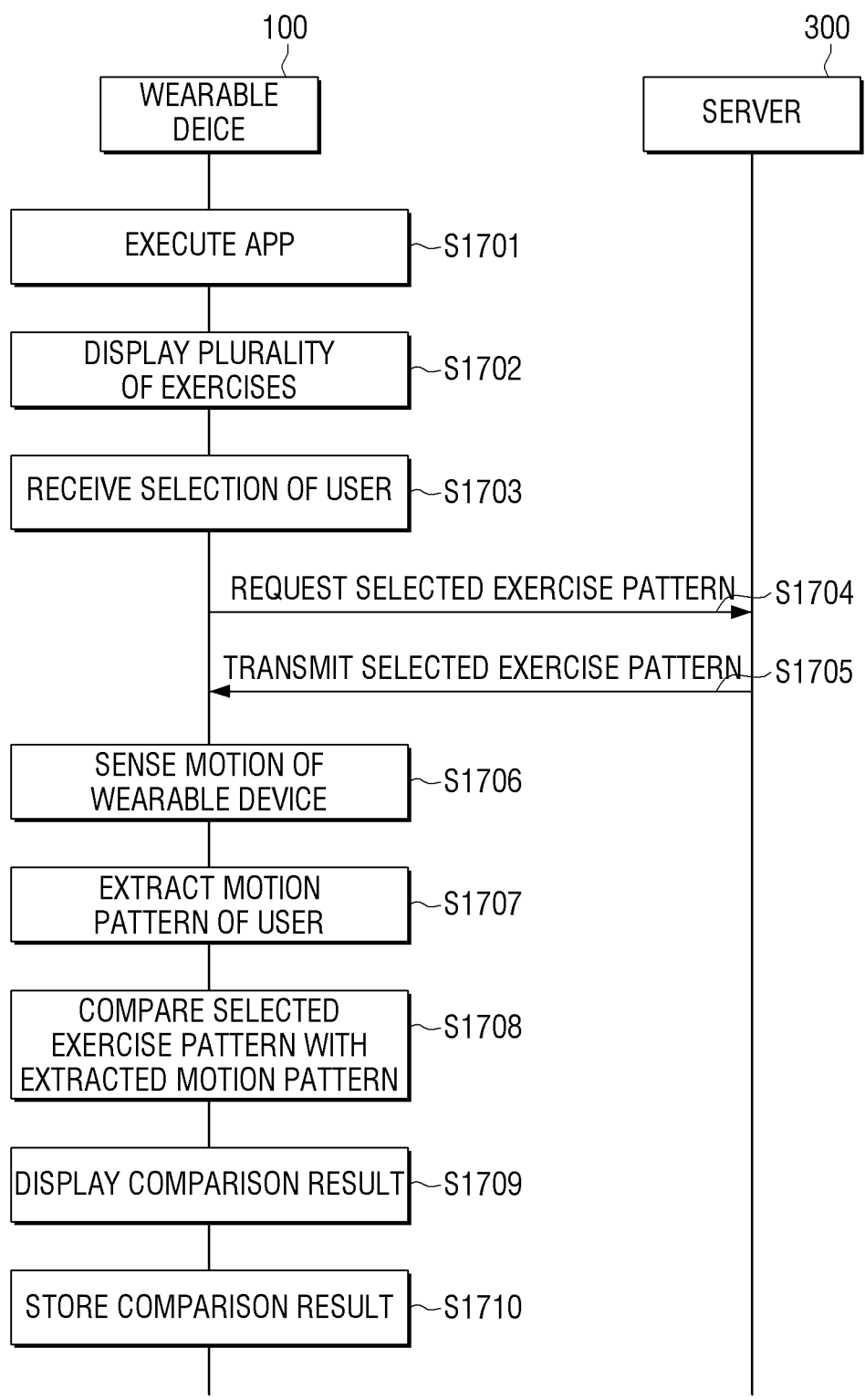
FIGS. 17 to 19 are flowcharts illustrating processes of measuring an exercise result to manage exercise of a user according to diverse exemplary embodiments of the present disclosure.

FIG. 17 is a flowchart illustrating a process of measuring an exercise result to manage exercise of a user according to an exemplary embodiment of the present disclosure. Specifically, FIG. 17 is a flowchart illustrating a process of measuring an exercise result in a case in which the wearable device includes the touch screen as the user interface.

Referring to FIG. 17, first, the user executes an exercise management application (hereinafter, referred to app) in the wearable device 100 (S1701). Next, the wearable device 100 displays a plurality of exercises (S1702). In this case, the plurality of displayed exercises may be those stored in the wearable device 100, or those received from the external device.

Next, the wearable device 100 receives a selection of the user (S1703). In this case, the user may select one exercise of the plurality of displayed exercises. Next, the wearable device 100 may request an exercise pattern corresponding to the exercise selected by the user to the server 300 (S1704). In this case, the server 300 may transmit the requested exercise pattern among a plurality of prestored exercise patterns to the wearable device 100 (S1705). In this case, although not illustrated, the wearable device 100 may display a right posture corresponding to the exercise selected by the user. Specifically, the wearable device 100 may display the right posture corresponding to the selected exercise through the user interface. In this case, the wearable device 100 may display a time limit and the target number of times in which the exercise is to be performed, together with the right posture corresponding to the selected exercise.

Meanwhile, for convenience of explanation, although the description is made that the exercise pattern corresponding to the selected exercise is transmitted to the wearable device 100 and the posture of the selected exercise is then present, the order may be arbitrary at the time of actual implementation.

Next, the wearable device 100 may present the posture of the exercise selected in the wearable device 100 and then sense a motion of the wearable device 100 (S1706). Specifically, the wearable device 100 may sense the motion of the wearable device 100 using a sensor included therein. In this case, if the wearable device 100 presents the right posture of the exercise selected in the wearable device 100 and a predetermined event then occurs, the wearable device 100 may measure the motion of the wearable device 100. In this case, the predetermined event may be a case in which a predetermined time has lapsed after presenting the posture, or the user performs an input or a touch using the wearable device 100 or the user interface of the wearable device 100.

Next, the wearable device 100 may extract a motion pattern of the user wearing the wearable device 100 based on the sensed motion information of the wearable device 100 (S1707).

Next, the wearable device 100 may compare the selected exercise pattern with the extracted motion pattern (S608). In this case, the selected exercise pattern may be an exercise pattern selected through the user interface included in the wearable device 100 and received from the server 300. In this case, the wearable device 100 may compare the selected exercise pattern with the extracted motion pattern, and count the number of times that the user performs the exercise. Meanwhile, a method for comparing the selected exercise pattern with the extracted motion pattern and counting the number of times that the user performs the exercise refers to FIG. 10.

Next, the wearable device 100 may display the comparison result on the user interface included therein (S1709). In this case, the comparison result may be the number of times that the user performs the exercise counted by comparing the selected exercise pattern with the extracted motion pattern. Meanwhile, the comparison result may be exercise effect information calculated based on biological signals of the user measured through a body contact sensor included in the wearable device 100. An exemplary embodiment in which the exercise effect information is included in the comparison result will be described below in detail with reference to FIG. 21.

Next, the wearable device 100 may store the received comparison result (S1710). Meanwhile, for convenience of explanation, although the comparison result is illustrated and described as being stored in the wearable device 100, the comparison result may also be transmitted to the server 300 and stored therein at the time of actual implementation. As described above, the number of times that the preselected exercise is performed is counted and recorded using the wearable device 100, thereby making it possible to more conveniently manage the exercise of the user.

Figure 18:
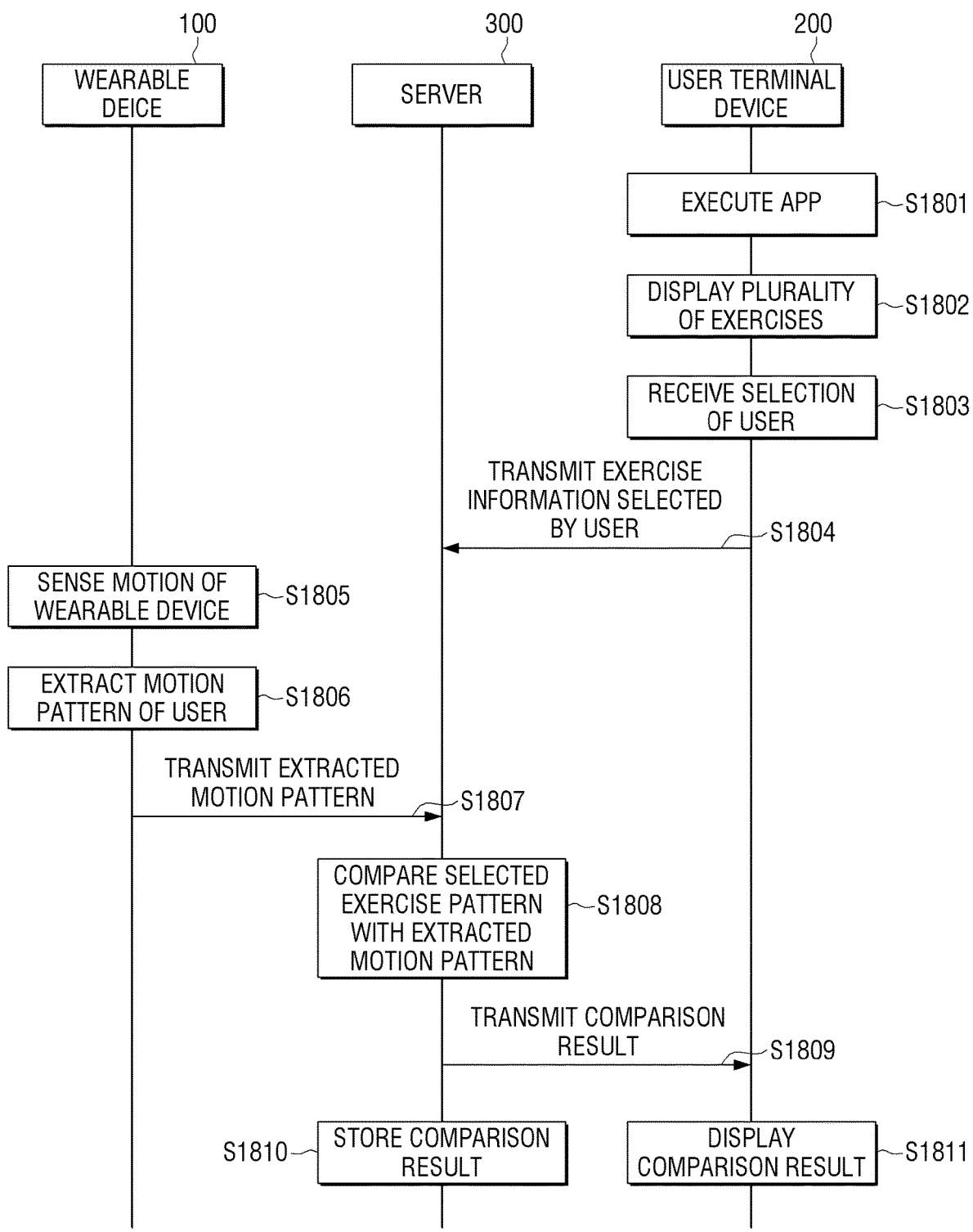

FIG. 18 is a flowchart illustrating a process of measuring an exercise result to manage exercise of a user according to an exemplary embodiment of the present disclosure. Specifically, FIG. 18 is a flowchart illustrating an example which may be implemented even in a case in which the wearable device 100 does not include the display.

Referring to FIG. 18, first, the user executes an exercise management application (hereinafter, referred to app) in the user terminal device 200 (S1801). Next, the user terminal device 200 displays a plurality of exercises (S1802). In this case, the plurality of displayed exercises may be those stored in the user terminal device 200, or those received from the external device.

Next, the user terminal device 200 receives a selection of the user (S1803). In this case, the user may select one exercise of the plurality of displayed exercises.

Hereinabove, although the method for selecting one exercise of the plurality of exercises by the user is described as being limited to selecting one exercise using the user terminal device 200, at the time of actual implementation, if the wearable device 100 includes a display, a method for limiting the exercise pattern to be compared with the motion pattern of the user by selecting the exercise in the same method may be implemented even in the wearable device 100.

Next, the user terminal device 200 transmits exercise information selected by the user to the server 300 (S1804). In this case, the exercise information may include at least one of exercise selected by the user and an exercise pattern corresponding to the exercise selected by the user. Specifically, if a plurality of exercise patterns corresponding to the plurality of exercises are stored in the server 300, the user terminal device 200 may transmit only the selection information of the user, and if the plurality of exercise patterns corresponding to the plurality of exercises are stored in the user terminal device 200 rather than the server 300, the user terminal device 200 may transmit the exercise pattern corresponding to the exercise selected by the user.

In this case, although not illustrated, the user terminal device 200 presents a right posture corresponding to the selected exercise. Specifically, the user terminal device 200 may display the right posture corresponding to the selected exercise through the user interface. Meanwhile, for convenience of explanation, although the user terminal device 200 is illustrated and described to present a posture of the selected exercise after transmitting the selected exercise information to the server 300, the order may be arbitrary at the time of actual implementation.

Next, the wearable device 100 may present the posture of the exercise selected in the user terminal device 200 and then sense a motion of the wearable device 100 (S1805). Specifically, the wearable device 100 may sense the motion of the wearable device 100 using a sensor included therein. In this case, if the wearable device 100 presents the right posture of the exercise selected in the user terminal device 200 and a predetermined event then occurs, the wearable device 100 may measure the motion of the wearable device 100. In this case, the predetermined event may be a case in which a predetermined time has lapsed after presenting the posture, or the user performs an input or a touch using the user interface of the wearable device 100 or the user terminal device 200.

Next, the wearable device 100 may extract a motion pattern of the user wearing the wearable device 100 based on the sensed motion information of the wearable device 100 (S1806).

Next, the wearable device 100 may transmit the extracted motion pattern information of the user to the server 300 (S1807). Meanwhile, for convenience of explanation, although the present disclosure is illustrated and described as being limited to the case in which the motion pattern information of the user is extracted from the wearable device 100 and is transmitted to the server 300, at the time of actual implementation, the present disclosure may be implemented in the form in which the wearable device 100 transmits only the sensed motion information of the wearable device 100 to the user terminal device 200 and extracts the motion pattern information of the user based on the motion information of the wearable device 100 received by the server 300.

Next, the server 300 may compare the exercise pattern corresponding to the selected exercise with the motion pattern of the user received from the wearable device 100 (S1808). In this case, the selected exercise pattern may be an exercise pattern received from the user terminal device 200. Meanwhile, the selected exercise pattern may be an exercise pattern corresponding to the exercise selected through the user interface included in the wearable device 100. In this case, the server 300 may compare the selected exercise pattern with the extracted motion pattern, and count the number of times that the user performs the exercise. Meanwhile, a method for comparing the selected exercise pattern with the extracted motion pattern and counting the number of times that the user performs the exercise refers to FIG. 10.

Next, the server 300 may transmit the comparison result to the user terminal device 200 (S1809). In this case, the comparison result may be the number of times that the user performs the exercise counted by comparing the selected exercise pattern with the extracted motion pattern. Meanwhile, the comparison result may be exercise effect information calculated based on biological signals of the user measured through a body contact sensor included in the wearable device 100. An exemplary embodiment in which the exercise effect information is included in the comparison result will be described below in detail with reference to FIG. 21.

In this case, the server 300 may store the comparison result in the storage (S1810).

Next, the user terminal device 200 receiving the comparison result from the wearable device 100 may display the received comparison result on the user interface included in the user terminal device 200 (S1811). Meanwhile, for convenience of explanation, although the comparison result is illustrated and described as being transmitted to the user terminal device 200 and displayed thereon, at the time of actual implementation, when the wearable deice 100 includes a touch screen as the user interface, the comparison result may be transmitted to the wearable device 100 and may be displayed on the touch screen included in the wearable device 100. As described above, the number of times that the preselected exercise is performed is counted and recorded using the wearable device 100, thereby making it possible to more conveniently manage the exercise of the user. Meanwhile, since the plurality of exercise patterns are stored in the server and the measured signals are processed in the server, the exercise management system according to the present disclosure may be implemented even in a case in which the wearable device 100 and the user terminal device 200 do not include a large capacity battery and a large capacity memory.

Figure 19:
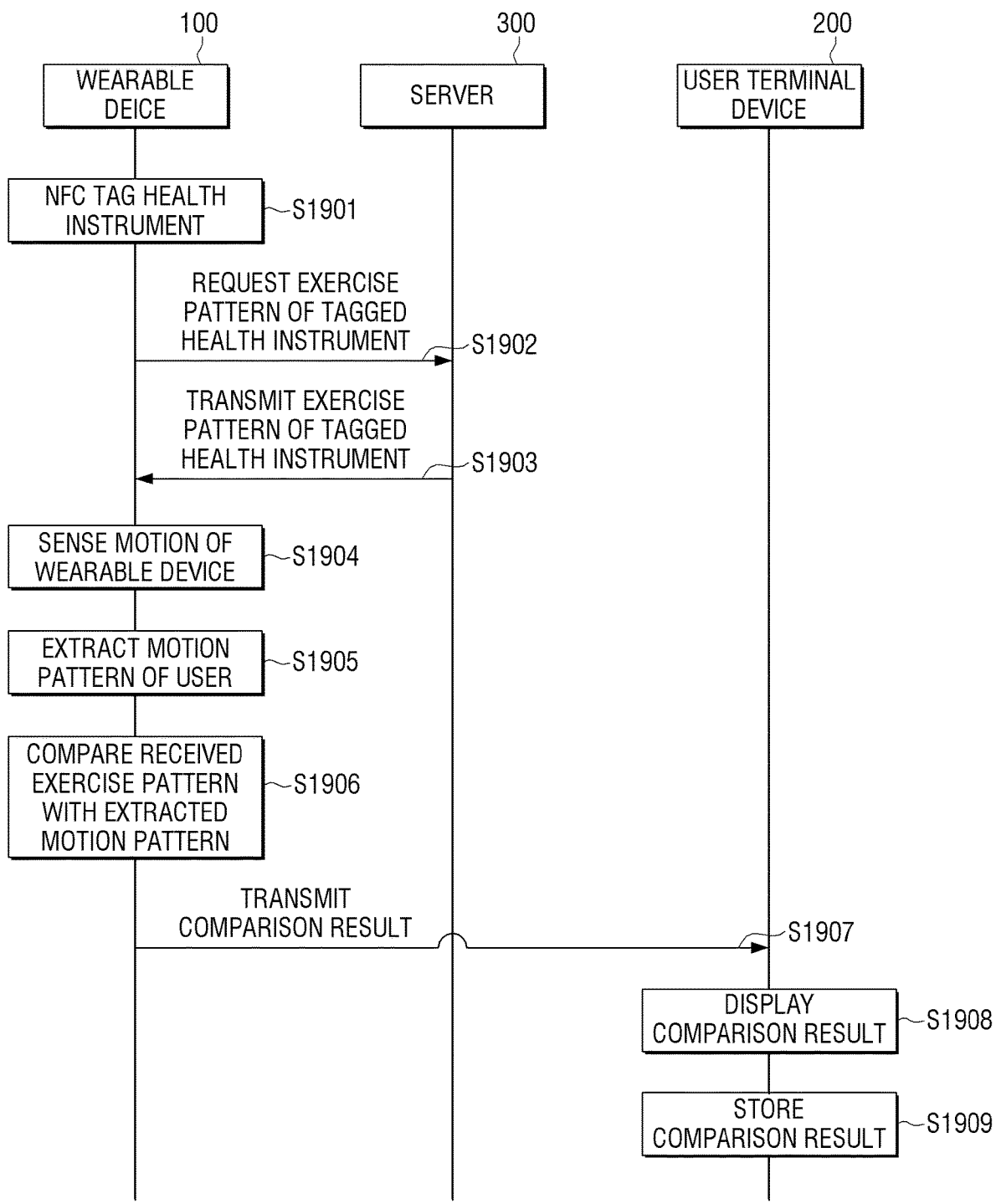

FIG. 19 is a flowchart illustrating a process of measuring an exercise result using a health instrument according to an exemplary embodiment of the present disclosure.

Referring to FIG. 19, first, the wearable device 100 including the NFC module is tagged with one health instrument of a plurality of health instruments on which the NFC tag is mounted (S1901). Next, the wearable device 100 may request an exercise pattern corresponding to the tagged health instrument to the server 300 (S1902). In this case, the server 300 may transmit the requested exercise pattern among a plurality of stored exercise patterns corresponding to the plurality of health instruments to the wearable device 100 (S1903). Specifically, the server 300 may transmit an exercise pattern corresponding to the tagged health instrument among the plurality of exercise patterns corresponding to the plurality of stored health instruments to the wearable device 100.

Next, the wearable device 100 may sense a motion of the wearable device 100 (S1904). Specifically, the wearable device 100 may sense the motion of the wearable device 100 using a sensor included therein. In this case, if the wearable device 100 is NFC tagged with one health instrument and a predetermined event then occurs, the wearable device 100 may measure the motion of the wearable device 100. In this case, the predetermined event may be a case in which a predetermined time has lapsed after the wearable device is NFC tagged, or the user performs an input or a touch using the user interface of the wearable device 100.

Next, the wearable device 100 may extract a motion pattern of the user wearing the wearable device 100 based on the sensed motion information of the wearable device 100 (S1905).

Next, the wearable device 100 may compare the received exercise pattern with the extracted motion pattern of the user (S1906). In this case, the received exercise pattern, which is received from the server 300, may be an exercise pattern corresponding to the tagged health instrument.

In this case, the wearable device 100 may compare the received exercise pattern with the extracted motion pattern, and count the number of times that the user performs the exercise. Meanwhile, a method for comparing the received exercise pattern with the extracted motion pattern and counting the number of times that the user performs the exercise refers to FIG. 10.

Next, the wearable device 100 may transmit the comparison result to the user terminal device 200 (S1907). In this case, the comparison result may be the number of times that the user performs the exercise, counted by comparing the received exercise pattern with the extracted motion pattern. Meanwhile, the comparison result may be exercise effect information calculated based on biological signals of the user measured through a body contact sensor included in the wearable device 100. An exemplary embodiment in which the exercise effect information is included in the comparison result will be described below in detail with reference to FIG. 21.

Next, the user terminal device 200 receiving the comparison result from the wearable device 100 may display the received comparison result on the user interface included in the user terminal device 200 (S1908). In this case, an example of a user interface window which may be displayed will be described below wither reference to FIG. 20. Meanwhile, for convenience of explanation, although the comparison result is illustrated and described as being transmitted to the user terminal device 200 and displayed thereon, at the time of actual implementation, when the wearable deice 100 includes a touch screen as the user interface, the comparison result may be transmitted to the wearable device 100 and may be displayed on the touch screen included in the wearable device 100. In this case, the user terminal device 200 may store the received comparison result in the storage (S1909). Meanwhile, the wearable device 100 may also transmit the comparison result to the server 300 to allow it to be stored in a storage of the server 300.

As described above, the exercise pattern to be compared with the motion pattern of the user may be limited by tagging the wearable device with the health instrument on which the NFC tag is mounted without a separate selection process in the wearable device and the user terminal device, and as a result, the number of the times that the user performs the exercise may be counted even in a case in which the user performs the exercise using the health instrument, thereby managing the exercise of the user.

As described above, the number of times that the preselected exercise is performed is counted and recorded using the wearable device 100, thereby making it possible to more conveniently manage the exercise of the user. Meanwhile, since the plurality of exercise patterns are stored in the server and the measured signals are processed in the server, the exercise management system according to the present disclosure may be implemented even in a case in which the wearable device 100 and the user terminal device 200 do not include a large capacity battery and a large capacity memory.

Figure 20:
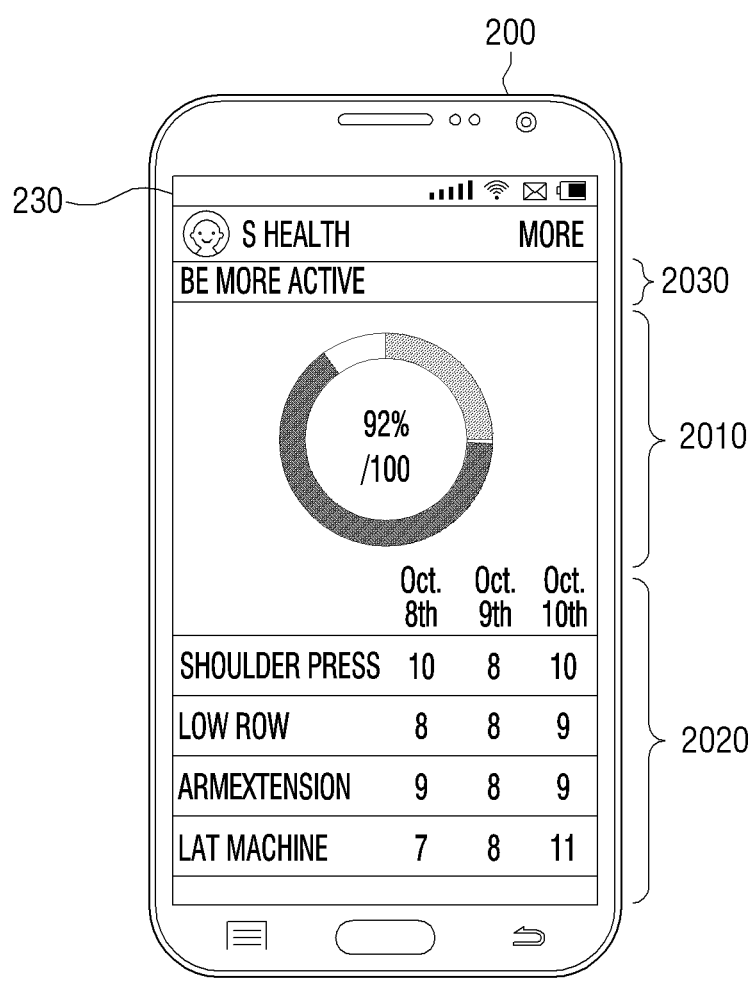

FIG. 20 is a diagram illustrating an example of an interface window providing a measured exercise result to the user according to an exemplary embodiment of the present disclosure.

Referring to FIG. 20, the interface window displayed on the user interface 230 included in the user terminal device 200 may include whether or not the target is reached according to an exercise measurement of the user 2010, the number of times that the user performs the exercise 2020, an evaluation according to the exercise measurement of the user 2030, and the like.

Specifically, whether or not the target is reached according to an exercise measurement of the user 2010 included in the interface window may be a ratio of a target reach determined by comparing the presented target number of times with the number of times that the user performs the exercise under a condition that the target number of times is 100%. Meanwhile, this is merely an example, and may be implemented in various schemes such as a graph, a histogram, and the like at the time of actual implementation.

Meanwhile, the number of times that the user performs the exercise 2020 included in the interface window may display the number of times of exercise performed for each date. Specifically, the number of times that the user performs the exercise 2020 included in the interface window may display the number of times of exercise performed in the health instrument for each date. In this case, each health instrument may be a health instrument selected by tagging, by the user, the wearable device among the plurality of health instruments on which the NFG tag is mounted. Meanwhile, the number of times of exercise performed in each health instrument may be the number of times that the user performs the exercise, counted according to an exemplary embodiment of the present disclosure.

Meanwhile, the evaluation according to the exercise measurement of the user 2030 included in the interface window may be displayed according to whether or not the present target is reached. For example, if the number of times that the user performs the exercise does not reach the presented target number of times, an evaluation such as 'be more active' may be displayed, and if the number of times that the user performs the exercise reaches the presented target number of times, an evaluation such as 'complete' or the like may be displayed. Meanwhile, this is merely an example, and may be implemented in various schemes. For example, an evaluation step may be set to three or more, or an evaluation phrase may be set.

Figure 21:
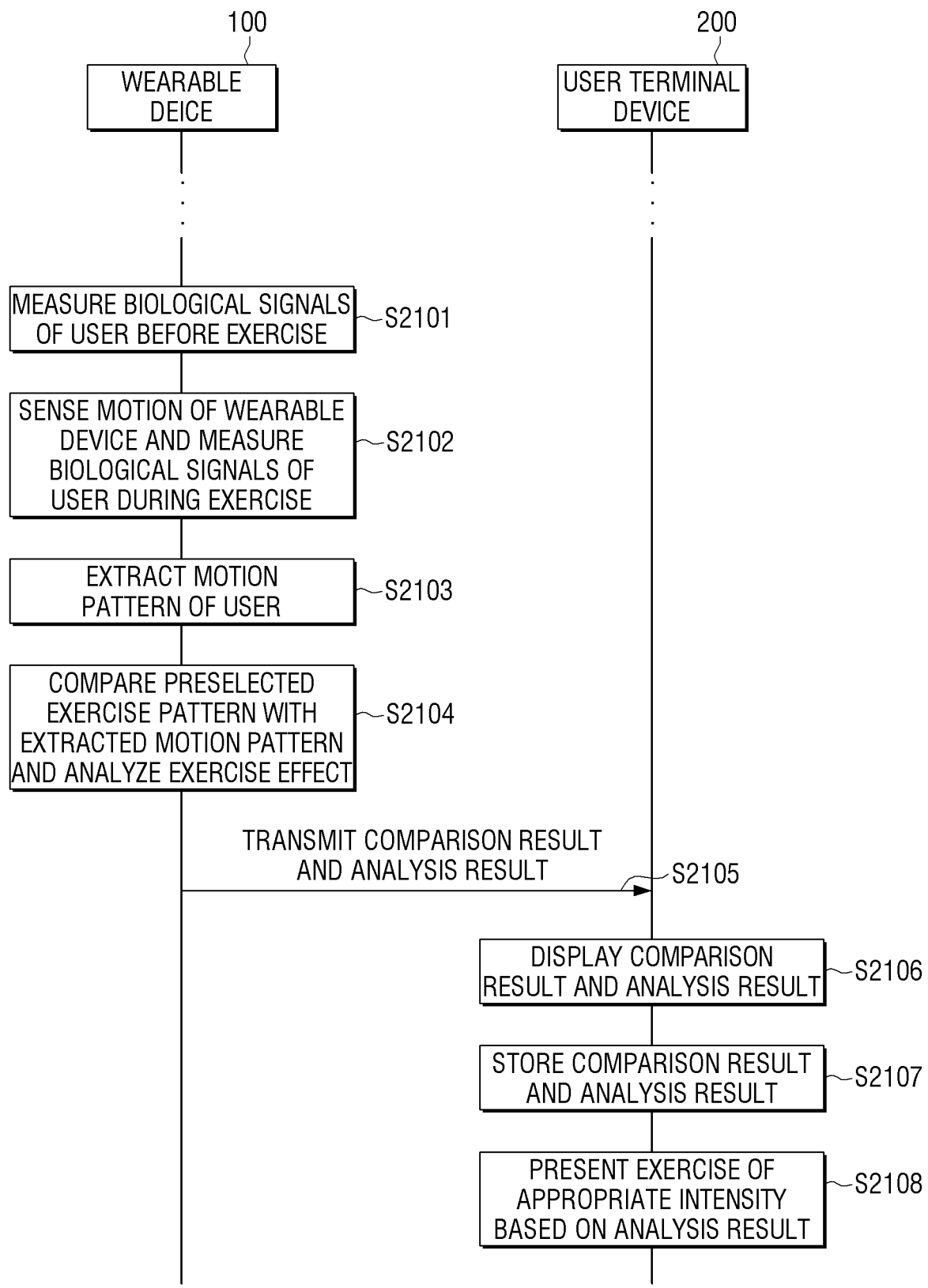
FIG. 21 is a flowchart illustrating a method for adjusting exercise intensity and presenting the adjusted exercise intensity according to an exemplary embodiment of the present disclosure.

FIG. 21 is a flowchart illustrating a method for adjusting exercise intensity and presenting the adjusted exercise intensity according to an exemplary embodiment of the present disclosure.

Referring to FIG. 21, first, although not illustrated, it is assumed that the user selects one exercise of the plurality of exercises in the wearable device 100 or the user terminal device 200, or tags the wearable device 100 with one health instrument of the plurality of health instruments on which the NFC tag is mounted to limit one exercise pattern to be compared with the motion pattern of the user.

In this case, the wearable device 100 may measure biological signals of the user before the user starts the selected exercise (S2101). Specifically, the wearable device 100 may measure the biological signals such as heartbeat, body temperature, and skin resistance of the user using a body contact sensor included therein.

Next, the wearable device 100 may sense a motion of the wearable device 100, and measure the biological signals of the user during the exercise (S2102). Specifically, if the user selects the exercise and a predetermined event then occurs, the wearable device 100 may sense the motion of the wearable device 100. In this case, if user selects the exercise and the predetermined event then occurs, the wearable device 100 may determined that the user is exercising and may measure the biological signals of the user. In this case, the predetermined event may be a case in which a predetermined time has lapsed after the exercise is selected by the user, or the user performs an input or a touch using the user interface of the wearable device 100 or the user terminal device 200.

Next, the wearable device 100 may extract a motion pattern of the user wearing the wearable device 100 based on the sensed motion information of the wearable device 100 (S2103).

Next, the wearable device 100 may compare an exercise pattern corresponding to the selected exercise with the extracted motion pattern of the user and analyze the exercise effect (S2104). In this case, the selected exercise pattern may be an exercise pattern corresponding to the exercise selected in the wearable device 100 or the user terminal device 200, or an exercise pattern corresponding to the health instrument selected by the user. In this case, the wearable device 100 may compare the exercise pattern corresponding to the selected exercise with the extracted motion pattern, and count the number of times that the user performs the exercise. Meanwhile, a method for comparing the selected exercise pattern with the extracted motion pattern and counting the number of times that the user performs the exercise refers to FIG. 10.

In this case, the wearable device 100 may analyze the exercise effect performed by the user based on the measured biological signals of the user. Specifically, the wearable device 100 may analyze the exercise effect performed by the user by measuring heartbeat, body temperature, and skin resistance of the user before and after the exercise. For example, the wearable device 100 may measure the heartbeat of the user and a variation in heartbeat before and after the exercise of the user using the sensor included therein. In this case, the wearable device 100 may analyze an amount of calorie consumption or the like using the measured biological signals.

Next, the wearable device 100 may transmit the comparison result and the analysis result to the user terminal device 200 (S2105). Specifically, the wearable device 100 may transmit the analysis result of the exercise effect such as the number of times that the user performs the preselected exercise, a variation in heartbeat, a variation in body temperature, a variation in skin resistance, an amount of calorie consumption, and the like to the user terminal device 200.

Next, the user terminal device 200 may display the received comparison result and analysis result (S2106). In this case, the user terminal device 200 may store the received comparison result and analysis result. Meanwhile, hereinabove, although the present disclosure is illustrated and described as being limited to the case in which the comparison result and the analysis result are displayed on and stored in the user terminal device 200, at the time of actual implementation, the comparison result and the analysis result may be stored in the wearable device 100 or the server, and if the wearable device 100 includes the touch screen as the user interface, the comparison result and the analysis result may be displayed on the wearable device 100.

Next, the user terminal device 200 may present exercise of appropriate intensity based on the analysis result (S2108). Specifically, the user terminal device 200 may modify and store the stored intensity of exercise based on the analysis result. Thereafter, if the user selects the same exercise, the user terminal device 200 may present exercise of the modified intensity to the user.

For example, if the measured variation in heartbeat does not reach a predetermined variation, the user terminal device 200 may determine that the presented exercise intensity is weak, and may increase and store exercise intensity to be presented by reducing a time limit or increasing the target number of times.

Meanwhile, hereinabove, although the present disclosure is illustrated and described as being limited to the case in which the user terminal device 200 adjusts the exercise intensity of the user according to the analysis result of the exercise effect, at the time of actual implementation, the adjustment of the exercise intensity may be performed by the wearable device 100 or the server. As described above, the number of times that the preselected exercise is performed is counted and recorded using the wearable device 100, thereby making it possible to more conveniently manage the exercise of the user. In addition, it is possible to effectively manage the exercise by adjusting the exercise intensity presented according to the exercise measurement result of the user.

Figure 22:
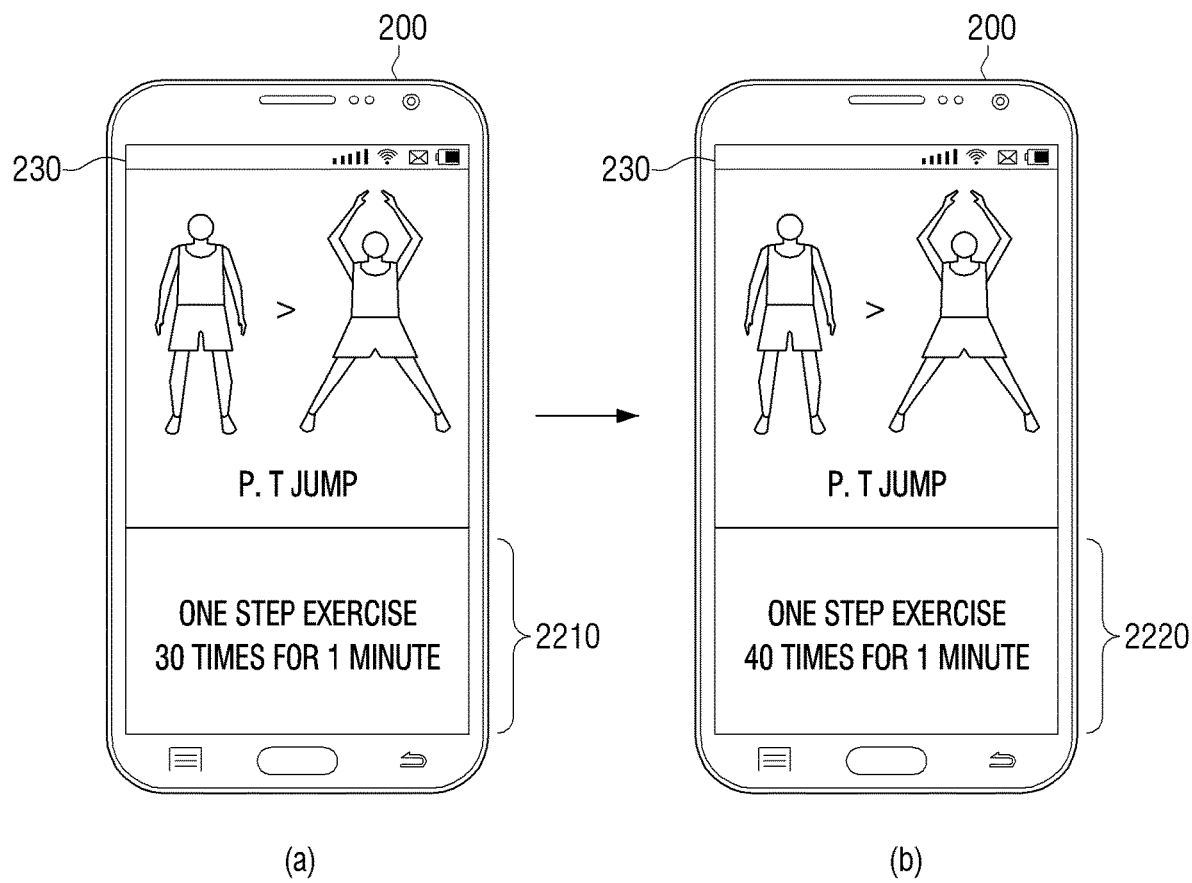
FIG. 22 is a diagram illustrating an example of adjusting and presenting the exercise intensity according to the method illustrated in FIG. 21.

FIG. 22 is a diagram illustrating an example of adjusting and presenting the exercise intensity according to the method illustrated in FIG. 21.

Referring to FIG. 22A, if the user selects the P.T jump among the plurality of exercises, the user interface 230 included in the user terminal device 200 may display a time limit and the target number of times 2210 in which the selected exercise is to be performed, together with a right posture in which the P. T jump is performed.

In this case, if the user completes the target number of times within the displayed time limit and a variation in biological signals of the user before and after the exercise does not reach a predetermined variation as a result of determining the exercise result based on the biological signals measured by the user terminal device 200, the user terminal device 200 may adjust the exercise intensity in a way in which the time limit is reduced or the target number of times is increased.

Referring to FIG. 22B, for example, if the variation in the biological signals of the user before and after the exercise does not reach the predetermined variation, the user terminal device 200 may increase the target number of times from 30 to 40, and thereafter, if the user selects the P. T jump, which is the same exercise, the user terminal device 200 may display the modified target number of times 2220.

Figure 23:
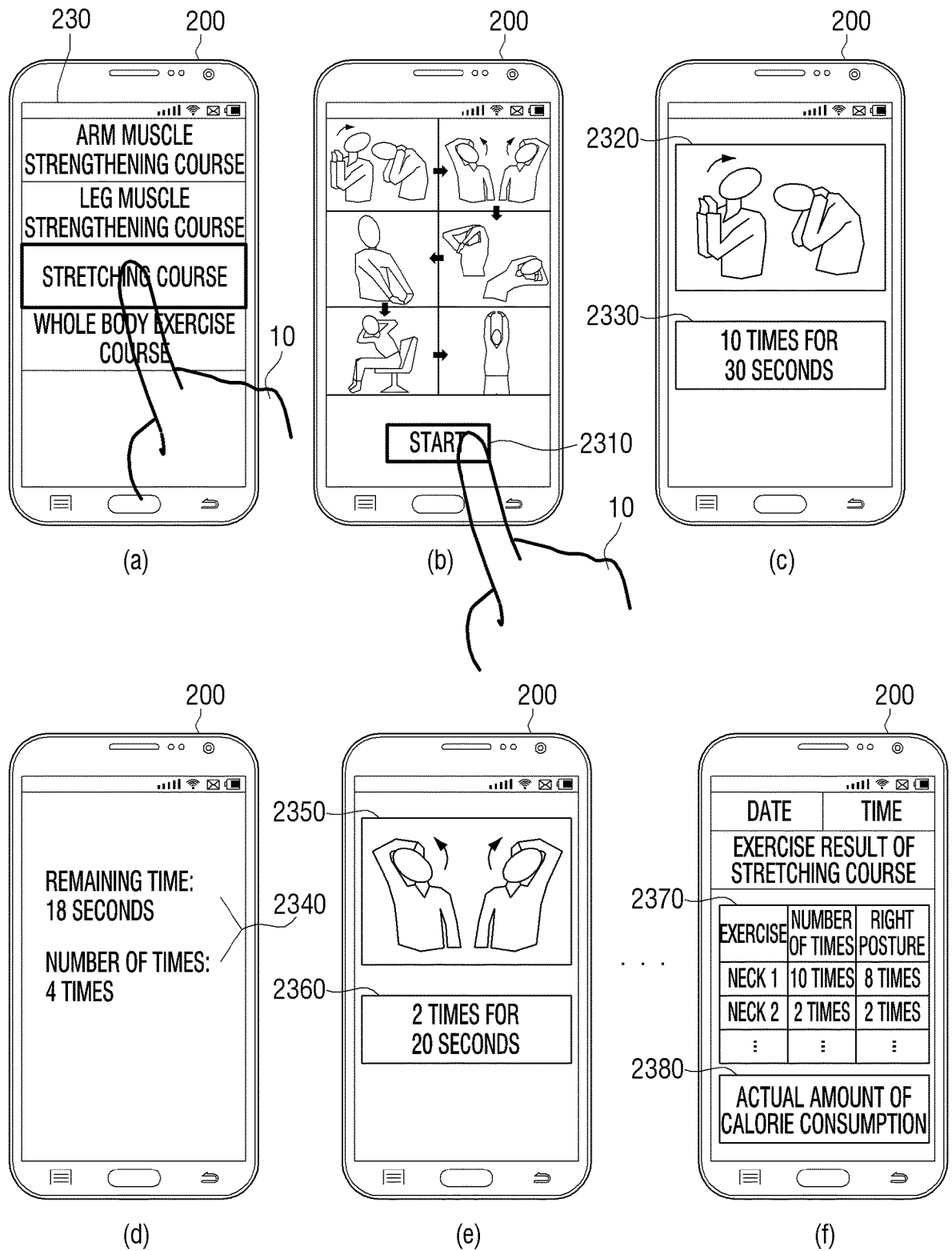
FIG. 23 is a diagram illustrating a method for presenting an exercise course and managing exercise of a user according to an exemplary embodiment of the present disclosure.

FIG. 23 is a diagram illustrating a method for presenting an exercise course and managing exercise of a user according to an exemplary embodiment of the present disclosure.

Hereinabove, the present disclosure has been described as being limited to the example in which the user selects one exercise of the plurality of exercises and the number of times that the user performs the selected exercise is counted. However, at the time of actual implementation, the present disclosure may be implemented in a way in which the user selects one exercise course of a plurality of exercise courses and the number of times that the user performs a plurality of exercises included in the selected exercise course is each counted.

Referring to FIG. 23A, the user 10 may select one exercise course of a plurality of exercise courses displayed on the user interface 230 included in the user terminal device 200.

If the user 10 selects a 'stretching course', which is one exercise course of the plurality of exercise courses, the user terminal device 200 may display postures and orders of a plurality of exercises included in the stretching course, as illustrated in FIG. 23B.

In this case, if a predetermined event occurs, the user terminal device 200 may display postures, time limits, and the target number of times of the plurality of exercises in the predetermined order.

Specifically, if the user 10 clicks a 'start' button 2310, the user terminal device 200 may display a right posture 2320 of a predetermined first neck stretching and may display the time limit and the target number of times 2330 (10 times for 30 seconds), as illustrated in FIG. 23C.

Thereafter, if a predetermined time has lapsed, or the user performs an input or a touch using the user interface, the user terminal device 200 may count and display the remaining time and the number of times that the user performs the displayed exercise 2340, as illustrated FIG. 23D. In this case, the user terminal device 200 may actuate a timer to increase the number of times that the user performs the displayed exercise for the time limit by one, or to display a total number of times counted after the time limit has lapsed. Meanwhile, the user terminal device 200 may also display the time taken to perform all the target number of times by the user.

If at least one of the lap of the time limit or the completion of the target number of times is satisfied, the user terminal device 200 may display a right posture 2350 of a predetermined second neck stretching and may display a time limit and the target number of times 2360 (two times for 20 seconds), as illustrated in FIG. 23E. Thereafter, although not illustrated, if the predetermined time has lapsed, or the user performs an input or a touch using the user interface, the user terminal device 200 may count and display the remaining time and the number of times that the user performs the displayed exercise.

As described above, if the plurality of exercises included in the selected exercise course are all performed according to the predetermined order, the user terminal device 200 may display the results 2370 and 2380 that the selected exercise course is performed. Specifically, the user terminal device 200 may display the number of times that the user performs the plurality of exercises included in the selected exercise course. In this case, the user terminal device 200 may determine an accuracy of the exercise performed by the user, and may count and display the number of times that the user performs the exercise in the right posture. Meanwhile, the user terminal device 200 may display an exercise effect 2380 calculated based on the biological signals of the user measured before and after the exercise according to an exemplary embodiment of the present disclosure.

Meanwhile, hereinabove, although the present disclosure is limited to the case in which the user terminal device 200 selects the exercise course and counts and displays the exercise performed by the user according to an exemplary embodiment of the present, at the time of actual implementation, if the wearable device includes the touch screen as the user interface, the wearable device may select the exercise course and count and display the exercise performed by the user. Meanwhile, the selection of the exercise course and the counting and displaying of the exercise performed by the user may be implemented using a button, a wheel, a dial, and the like included in the wearable device.

Figure 24:
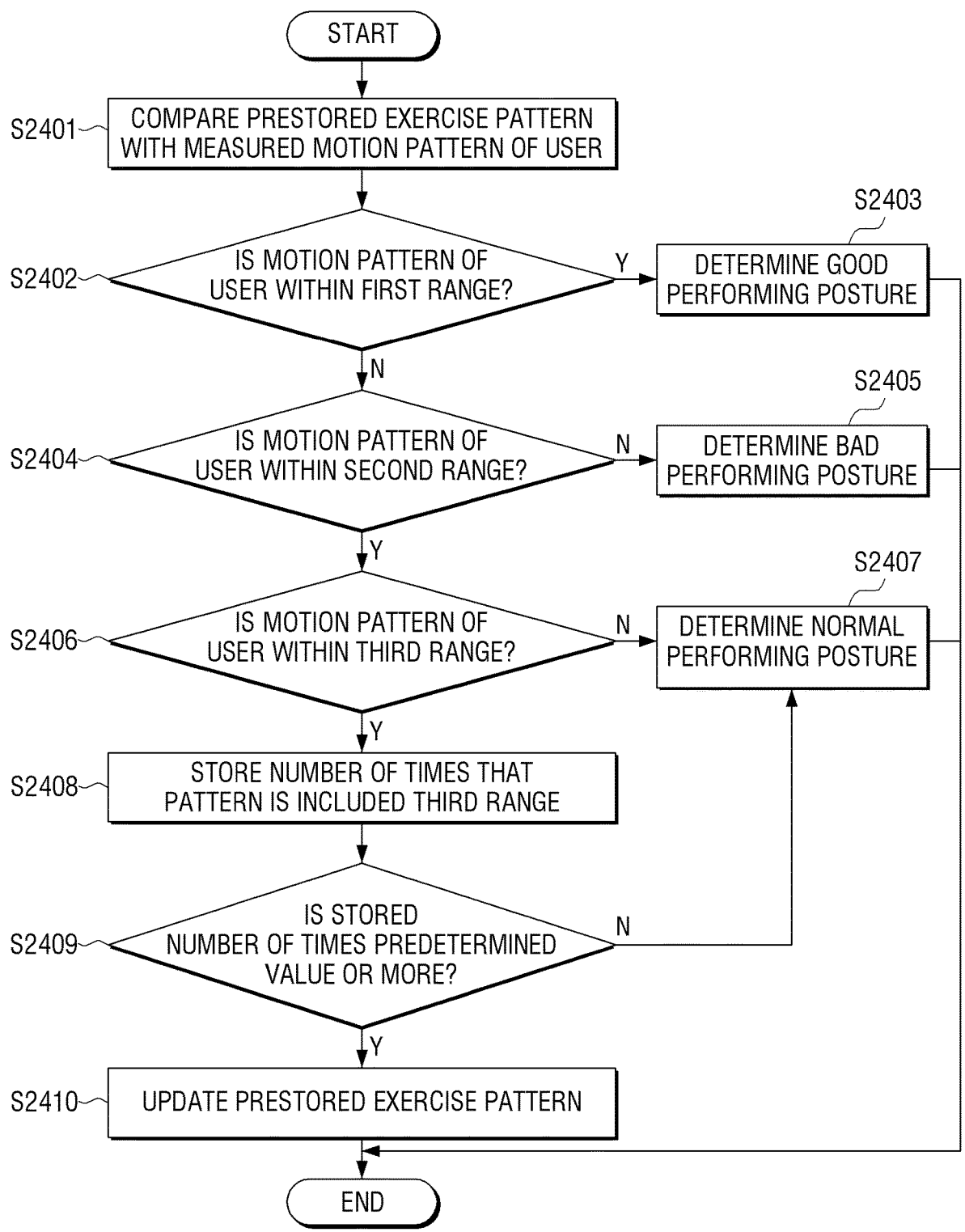
FIG. 24 is a flowchart illustrating a method for updating a tailored motion pattern for a user based on a motion pattern of the user measured according to an exemplary embodiment of the present disclosure.

FIG. 24 is a flowchart illustrating a method for updating a tailored motion pattern for a user based on a motion pattern of the user measured according to an exemplary embodiment of the present disclosure.

Referring to FIG. 24, although not illustrated, first, it is assumed that the user selects one exercise of the plurality of exercises in the wearable device 100 or the user terminal device 200, or tags the wearable device 100 with one health instrument of the plurality of health instruments on which the NFC tag is mounted to limit one exercise pattern to be compared with the motion pattern of the user.

In this case, the wearable device may compare a prestored exercise pattern with the measured motion pattern of the user (S2401). In this case, the prestored exercise pattern may mean an exercise pattern corresponding to the exercise selected by the user among a plurality of prestored exercise patterns. Meanwhile, the measured motion pattern of the user may be motion pattern information of the user extracted from motion information of the wearable device sensed in the wearable device.

Next, the wearable device may determine whether or not the motion pattern of the user is within a first range (S2402). In this case, the first range may mean a case in which when the prestored exercise pattern and the motion pattern of the user are compared with each other, it is determined that the user completes the presented posture within the time limit. For example, the first range may be a case in which the motion pattern of the user is a first pattern 1211 of a motion pattern 1210 of the user illustrated in FIG. 12. In this case, if it is determined that the motion pattern of the user is within the first range (S2402-Y), the wearable device may determine that an operation performed by the user is a good performing posture (S2403).

However, if the motion pattern of the user does not correspond to the first range (S2402—N), the wearable device may determine whether or not the motion pattern of the user corresponds to a second range (S2404). In this case, the second range may be a case in which when the prestored exercise pattern and the motion pattern of the user are compared with each other, a noise pattern appears in the motion pattern of the user, or it takes more time to perform the presented target number of times than the time limit. For example, the second range may be a case in which the motion pattern of the user is a third pattern 1212 or a fourth pattern 1213 of a motion pattern information 1210 of the user illustrated in FIG. 12. In this case, if it is determined that the motion pattern of the user does not correspond to the second range (S2404—N), the wearable device may determine the operation performed by the user as a bad performing posture (S2405). Specifically, if the motion pattern of the user does not correspond to both the first range and the second range, the wearable device may determine that the operation performed by the user is not an operation of the preselected exercise and may not count the operation performed by the user.

However, if the motion pattern of the user corresponds to the second range (S2404—Y), the wearable device may determine whether or not the motion pattern of the user corresponds to a third range (S2406). In this case, the third range may be a case in which the motion pattern of the user is included in the second range, but is slightly out of the first range. Specifically, the third range may be a case in which an operation corresponding to the motion pattern of the user corresponds to a normal performing posture, but is slightly out of a range of the good performing posture. In this case, the third range may be a case in which it is slightly out of the time limit present to perform the selected exercise by the user. For example, the third range may be a case in which it is presented to the user to perform the selected exercise is performed once for 5 seconds, but the user takes 6 seconds to perform the same operation once. In this case, the third range may be changed by a setting of the user.

If the motion pattern of the user does not correspond to the third range (S2406-N), the wearable device may determine that the operation corresponding to the motion pattern of the user is the normal performing posture (S2407). However, if the motion pattern of the user is included in the third range (S2406—Y), the wearable device may store the number of times that the motion pattern of the user is included in the third range (S2408). Next, the wearable device may determine whether or not the number of times that the motion pattern of the user is included in the third range is a predetermined value or more (S2409). If the stored number of times is less than the predetermined value (S2409—N), the wearable device may determine that the operation corresponding to the motion pattern of the user is the normal performing posture. However, if the number of times that the motion pattern of the user is included in the third range is the predetermined value or more (S2409—Y), the wearable device may update the prestored exercise pattern compared with the motion pattern of the user (S2410). Specifically, the wearable device may modify the prestored exercise pattern to the motion pattern of the user which is included in the third range as many as the predetermined number of times or more, and may again store it. As described above, by updating the exercise pattern which is uniformly stored to the exercise pattern which is suit the user, exercise intensity which is suit the user may be presented and the exercise of the user may be effectively managed.

Meanwhile, hereinabove, although the present disclosure is described as being limited to a case in which the exercise pattern prestored in the wearable device is updated to be suited to the user, at the time of actual implementation, the user terminal device or the server in which the plurality of exercise patterns are stored may update the prestored exercise pattern.

As described above, according to the diverse exemplary embodiments of the present disclosure, the exercise of the user may be effectively managed by counting the number of times that the user performs the exercise and calculating the exercise effect using an existing wearable device.

The methods according to the exemplary embodiments of the present disclosure may be implemented in a form of a program instruction that may be performed through various computer means and may be recorded in a computer-readable medium. The computer-readable medium may include program instructions, data files, data structure, or the like, alone or a combination thereof. For example, the computer-readable medium may be stored in a volatile or non-volatile storage medium such as a storage device of ROM or the like, or for example, a memory such as RAM, a memory chip, an apparatus or a integrated circuit, or for example, an optically or magnetically recordable and machine (e.g., a computer) readable storage medium such as CD, DVD, a magnetic disk, a magnetic tape, or the like, irrespective of whether or not it is removable or rewritable. It may be appreciated that a memory which may be included in a mobile terminal is an example of a machine readable storage medium suitable for storing a program or programs including instructions that implement the exemplary embodiments of the present disclosure. The program instructions recorded in the medium may be those which are designed and constituted especially for the present disclosure, or may also be those which are known to those skilled in a field of computer software and are usable.

As described above, although the present disclosure is described with reference to the limited exemplary embodiments and the drawings, the present disclosure is not limited to the above exemplary embodiments and may be variously changed and modified from the description by a person skilled in the art to which the present disclosure pertains.

Accordingly, the scope of the present disclosure is not construed as being limited to the described exemplary embodiments, but is defined by the appended claims as well as equivalents thereto.

The invention claimed is:

1. A wearable device comprising:
   a memory storing at least one exercise pattern, each of the at least one exercise pattern comprising a pattern of a type of exercise;
   a sensor configured to sense a motion of the wearable device; and
   at least one processor configured to:
   receive a user input selecting an exercise pattern for an exercise,
   based on the user input, select the exercise pattern from among the stored at least one exercise pattern,
   obtain motion information of the wearable device sensed through the sensor,
   determine a motion pattern corresponding to an operation performed by a user based on the obtained motion information,
   based on the motion pattern being within a first range related to the selected exercise pattern, determine that the operation performed by the user is a first posture,
   identify whether the motion pattern is within a third range related to the selected exercise pattern based on the motion pattern being within a second range and the motion pattern being out of the first range,
   identify a number of the motion pattern based on the motion pattern being within the third range,
   based on the number of the motion pattern being less than a predetermined number, determine that the operation performed by the user is a second posture, and
   based on the number of the motion pattern being greater than or equal to the predetermined number, update the selected exercise pattern based on the motion pattern.

2. The wearable device of claim 1, wherein the at least one processor is further configured to determine an accuracy of the exercise.

3. The wearable device of claim 1,
   wherein the first posture is a posture which the user completes an operation related to the exercise pattern within a predetermined time, and
   wherein the second posture is a posture of which the motion pattern comprises a noise pattern or a posture which the user does not complete an operation related to the exercise pattern within the predetermined time.

4. The wearable device of claim 1, further comprising a user interface configured to select at least one exercise and display a number of times that the at least one exercise is performed.

5. The wearable device of claim 4, wherein the user interface is further configured to display the number of times that the at least one exercise is performed together with a prestored target number of times.

6. The wearable device of claim 5, wherein the at least one processor is further configured to modify the prestored target number of times based on the number of times that the at least one exercise is performed for a predetermined time.

7. The wearable device of claim 1, further comprising:
a communicator configured to receive exercise information from an external device,
wherein the at least one processor is further configured to compare an exercise pattern corresponding to the exercise information with the motion pattern.

8. The wearable device of claim 7, wherein the exercise information includes at least one exercise pattern selected by a user.

9. The wearable device of claim 7, wherein the at least one processor is further configured to control the communicator to transmit the number of the motion pattern to the external device.

10. The wearable device of claim 7, wherein the communicator includes near field communication (NFC) circuitry communicable with an NFC tag.

11. The wearable device of claim 1, wherein the sensor includes at least one of a three-axis acceleration sensor or a gyro sensor.

12. The wearable device of claim 1, further comprising:
a body contact sensor configured to measure biological signals of the user,
wherein the at least one processor is further configured to calculate an exercise effect of the exercise based on the biological signals of the user measured by the body contact sensor.

13. The wearable device of claim 12, wherein the body contact sensor includes at least one of a heartbeat measuring sensor, a body temperature measuring sensor, or a skin resistance sensor.

14. A user terminal device connectable to a wearable device, the user terminal device comprising:
a memory storing at least one exercise pattern, each of the at least one exercise pattern comprising a pattern of a type of exercise;
a communicator configured to receive, from the wearable device, motion information and a user input selecting an exercise pattern for an exercise; and
a processor configured to:
based on the user input, select the exercise pattern from among the stored at least one exercise pattern,
determine a motion pattern of the wearable device corresponding to an operation performed by a user using the motion information,
based on the motion pattern being within a first range related to the selected exercise pattern, determine that the operation performed by the user is a first posture,
identify whether the motion pattern is within a third range related to the selected exercise pattern based on the motion pattern being within a second range and the motion pattern being out of the first range,
identify a number of the motion pattern based on the motion pattern being within the third range,
based on the number of the motion pattern being less than a predetermined number, determine that the operation performed by the user is a second posture, and
based on the number of the motion pattern being greater than or equal to the predetermined number, update the selected exercise pattern based on the motion pattern.

15. The user terminal device of claim 14, wherein the processor is further configured to determine an accuracy of the exercise.

* * * * *